US008362045B2

(12) United States Patent
Barre et al.

(10) Patent No.: US 8,362,045 B2
(45) Date of Patent: Jan. 29, 2013

(54) 5,6-DIARYL PYRIDINES SUBSTITUTED IN THE 2- AND 3-POSITION, PREPARATION THEREOF AND THERAPEUTIC USE THEREOF

(75) Inventors: Lionel Barre, Paris (FR); Christian Congy, Paris (FR); Philippe Pointeau, Paris (FR); Murielle Rinaldi-Carmona, Paris (FR)

(73) Assignee: Sanofi, Paris (FR)

( * ) Notice: Subject to any disclaimer, the term of this patent is extended or adjusted under 35 U.S.C. 154(b) by 141 days.

(21) Appl. No.: 12/755,883

(22) Filed: Apr. 7, 2010

(65) Prior Publication Data

US 2010/0256202 A1 Oct. 7, 2010

Related U.S. Application Data

(63) Continuation of application No. PCT/FR2008/001421, filed on Oct. 10, 2008.

(30) Foreign Application Priority Data

Oct. 12, 2007 (FR) .................................... 07 07186

(51) Int. Cl.
*A61K 31/44* (2006.01)
*C07D 9/02* (2006.01)
(52) U.S. Cl. .................. 514/357; 546/337; 546/335
(58) Field of Classification Search .................. 514/357; 546/337, 335
See application file for complete search history.

(56) References Cited

U.S. PATENT DOCUMENTS 5,916,905 A * 6/1999 Weier et al. .................... 514/345

FOREIGN PATENT DOCUMENTS

| WO | WO 02/055502 | 7/2002 |
|---|---|---|
| WO | WO 03/082191 | 10/2003 |
| WO | WO 2004/111034 | 12/2004 |
| WO | WO 2006/042955 | 4/2006 |
| WO | WO 2006/113704 | 10/2006 |

OTHER PUBLICATIONS

Rinaldi-Carmona, M., et al., SR147778 [5-(4-Bromophenyl)-1-(2,4-Dichlorophenyl)-4-ethyl-N-(1-Piperidinyl)-1H-Pyrazole-3-Carboxamide], A New Potent and Selective Antagonist of the CB1 Cannabinold Receptor: Biochemical and Pharmacological Characterization The Journal of Pharmacology and Experimental Therapeutics, vol. 310, No. 3, (2004), pp. 905-914.

Bouaboula, M., et al., A Selective Inverse Agonist for Central Cannabinold Receptor Inhibits Mitogen-Activated Protein Kinase Activation Stimulated by insulin or Insulin-Like Growth Factor 1, The Journal of Biological Chemistry, vol. 272, No. 35, (1997), pp. 22330-22339.

Bouaboula, M., et al., Stimulation of Cannabinold Receptor CB1 induces Krox-24 Expression in Human Astrocytoma Cells, The Journal of Biological Chemistry, vol. 270, No. 23, (1995), pp. 13973-13080.

Rinaldi-Carmona, M., et al., Biochemical and Pharmacological Characterisation of SR141716A, The First Potent and Selective Brain Cannabinold Receptor Antagonist, Life Sciences, vol. 56, No. 23/24, pp. 1941-1947, (1995).

Rinaldi-Carmona, M., et al., Characterization of Two Cloned Human CB1 Cannabinold Receptor isoforms, The Journal of Phamacology and Experimental Therapeutics, vol. 278, No. 2, pp. 671-878, (1996).

Rinaldi-Carmona, M., et al., SR141716A, A Potent and Selective Antogonist of the Brain Cannabinold Receptor, Febs Letters, vol. 350, (1994) pp. 240-244.

* cited by examiner

*Primary Examiner* — Rei-tsang Shiao
(74) *Attorney, Agent, or Firm* — Scully, Scott, Murphy & Presser, P.C.

(57) ABSTRACT

The invention relates to compounds corresponding to formula (I):

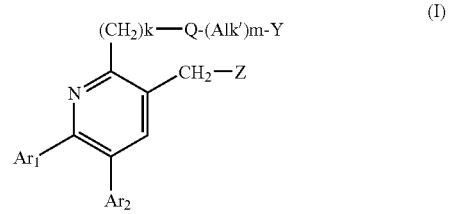

In which $Ar_1$, $Ar_2$, Q, Y, Z, Alk', k and m are as defined herein. The invention further relates to their preparations, intermediates therefor and their therapeutic uses.

15 Claims, No Drawings

5,6-DIARYL PYRIDINES SUBSTITUTED IN THE 2- AND 3-POSITION, PREPARATION THEREOF AND THERAPEUTIC USE THEREOF

CROSS REFERENCE TO RELATED APPLICATIONS

This application is a continuation of International application No. PCT/FR2008/001,421, filed Oct. 10, 2008, which is incorporated herein by reference in its entirety; which claims the benefit of priority of French patent application Ser. No. 07/07,186, filed Oct. 12, 2007.

The present invention relates to pyridine derivatives, to their preparation and to their therapeutic application.

International patent application WO 03/082 191 describes pyridine derivatives of formula:

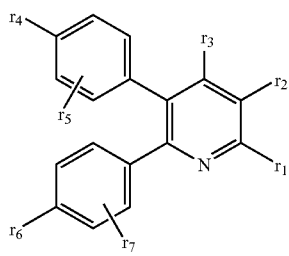

(1)

in which the substituents $r_1$ to $r_7$ have different values.

U.S. Pat. No. 5,916,905 describes pyridine derivatives of formula:

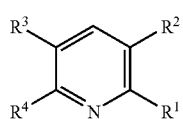

(2)

in which $R^3$ and $R^4$ may represent an aryl group and $R^2$ may represent an alkylcarbonylaminoalkyl group.

Patent application WO 2002/055 502 describes compounds of formula:

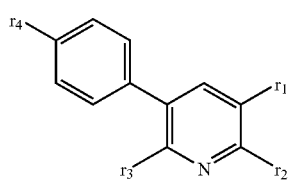

(3)

Patent application WO2006/113 704 describes compounds of formula:

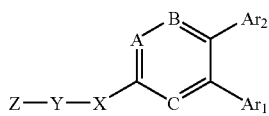

in which B may represent a nitrogen atom, and A and C represent carbon atoms.

Patent application WO 2004/111 034 describes pyrazine derivatives of formula:

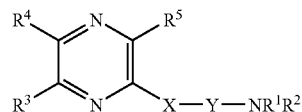

These compounds are described as being $CB_1$ receptor modulators.

Patent application WO 2006/042 955 describes pyridine derivatives that are cannabinoid $CB_1$ receptor antagonists, of formula:

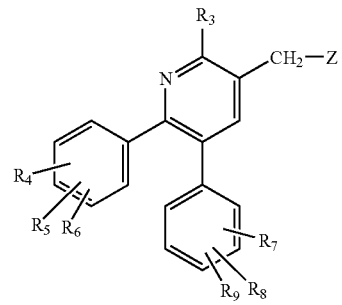

Novel 5,6-diarylpyridine derivatives bearing particular substituents in position 2 and 3, which have antagonist properties on the cannabinoid $CB_1$ receptors at the central and/or peripheral level, have now been found.

One subject of the present invention is compounds corresponding to the formula:

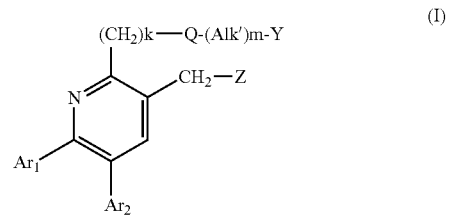

(I)

in which:
  Q represents an oxygen atom, a sulfur atom or a radical —$NR_1$— in which $R_1$ represents a hydrogen atom or a group $(C_1\text{-}C_4)$alkyl;
  Z represents a group —$N(R_3)XR_4$, —$N(R_3)COOR_5$ or —$OCON(R_3)R_5$;
  X represents a group —CO—, —$SO_2$—, —$CON(R_6)$— or —$CSN(R_6)$—;
  $R_3$ represents a hydrogen atom or a group $(C_1\text{-}C_4)$alkyl;
  $R_4$ represents:
    a group $(C_3\text{-}C_{10}$alkyl, which is unsubstituted or substituted with a group $CF_3$;
    a non-aromatic $(C_3\text{-}C_{12})$ carbocyclic radical, which is unsubstituted or substituted one or more times with identical or different substituents chosen from a group $(C_1\text{-}C_4)$alkyl, hydroxyl, $(C_1\text{-}C_4)$alkoxy, $(C_1\text{-}C_4)$alkylthio or cyano;

a saturated or unsaturated, oxygen-bearing, sulfur-bearing or nitrogen-bearing heterocyclic radical of 3 to 8 atoms, which is unsubstituted or substituted with one or more identical or different substituents chosen from a halogen atom, a group $(C_1$-$C_4)$alkyl, hydroxyl, trifluoromethyl, $(C_1$-$C_4)$alkoxy, trifluoromethoxy, trifluoromethylthio, $(C_1$-$C_4)$alkylthio, cyano, nitro and an oxo group;

an indolyl which is unsubstituted or substituted with a halogen atom or a group $(C_1$-$C_4)$alkyl, trifluoromethyl, hydroxyl, $(C_1$-$C_4)$alkoxy, trifluoromethoxy, trifluoromethylthio, $(C_1$-$C_4)$alkylthio, cyano or nitro;

a tetrahydronaphthyl; a naphthyl;

a benzothiophenyl or a benzofuryl;

a phenyl which is unsubstituted or substituted one or more times with identical or different substituents chosen from a halogen atom, a group $(C_1$-$C_4)$alkyl, trifluoromethyl, trifluoromethoxy, hydroxyl, $(C_1$-$C_4)$ alkoxy, $(C_1$-$C_4)$alkylthio, trifluoromethylthio, cyano, nitro, $(C_1$-$C_4)$alkanoyl, phenyl or a group $S(O)_n$Alk, $OS(O)_n$Alk or $NR_7R_8$;

a benzodioxyl;

a phenoxymethylene or a 1-phenoxyethylene, the phenyl groups being unsubstituted or substituted one or more times with identical or different substituents chosen from a halogen atom, a group $(C_1$-$C_4)$alkyl, trifluoromethyl, trifluoromethoxy, hydroxyl, $(C_1$-$C_4)$ alkoxy, $(C_1$-$C_4)$alkylthio, trifluoromethylthio, cyano, nitro, $(C_1$-$C_4)$alkanoyl, phenyl or a group $S(O)_n$Alk, $OS(O)_n$Alk or $NR_7R_8$; the methylene or ethylene groups being unsubstituted or substituted one or more times with identical or different substituents chosen from a group $(C_1$-$C_4)$alkyl or with a $(C_3$-$C_7)$cycloalkyl;

a phenylcyclopropyl, the phenyl group being unsubstituted or substituted one or more times with identical or different substituents chosen from a halogen atom, a group $(C_1$-$C_4)$alkyl, trifluoromethyl, trifluoromethoxy, hydroxyl, $(C_1$-$C_4)$alkoxy, $(C_1$-$C_4)$alkylthio, trifluoromethylthio, cyano, nitro, $(C_1$-$C_4)$alkanoyl, phenyl or a group $S(O)_n$Alk, $OS(O)_n$Alk or $NR_7R_8$;

a $(C_1$-$C_2)$alkylene substituted with one or two identical or different substituents chosen from:

(i) a $C_3$-$C_{12}$ non-aromatic carbocyclic radical which is unsubstituted or substituted one or more times with a group $(C_1$-$C_4)$alkyl, which may be identical or different;

(ii) a phenyl which is unsubstituted or substituted with one or more substituents, which may be identical or different, chosen from a halogen atom, a group $(C_1$-$C_4)$alkyl, hydroxyl, trifluoromethyl, $(C_1$-$C_4)$ alkoxy, $(C_1$-$C_4)$alkylthio, trifluoromethoxy, trifluoromethylthio, $(C_1$-$C_4)$alkanoyl, cyano, nitro, phenyl or a group $S(O)_n$Alk, $OS(O)_n$Alk or $NR_7R_8$;

(iii) a saturated or unsaturated, oxygen-bearing, sulfur-bearing or nitrogen-bearing heterocyclic radical of 3 to 8 atoms, which is unsubstituted or substituted with one or more substituents, which may be identical or different, chosen from a halogen atom, a group $(C_1$-$C_4)$alkyl, hydroxyl, trifluoromethyl, $(C_1$-$C_4)$alkoxy, trifluoromethoxy, trifluoromethylthio, $(C_1$-$C_4)$alkylthio, cyano or nitro;

furthermore, when X represents a group —$CON(R_6)$— or —$CSN(R_6)$—, $R_4$ may represent a group $(C_1$-$C_6)$ alkanoyl or a benzoyl or benzylcarbonyl group, the phenyl group of the said groups being unsubstituted or substituted with one or more identical or different substituents chosen from a halogen atom, a group $(C_1$-$C_4)$alkyl, trifluoromethyl, trifluoromethoxy, hydroxyl, $(C_1$-$C_4)$alkoxy, $(C_1$-$C_4)$alkylthio, trifluoromethylthio, cyano, nitro, $(C_1$-$C_4)$alkanoyl, phenyl or a group $S(O)_n$Alk, $OS(O)_n$Alk or $NR_7R_8$;

$R_5$ represents a phenyl which is unsubstituted or substituted one or more times with identical or different substituents chosen from a halogen atom or a group $(C_1$-$C_4)$ alkyl, trifluoromethyl, trifluoromethoxy, cyano, nitro, $(C_1$-$C_4)$alkoxy, $(C_1$-$C_4)$alkylthio, trifluoromethylthio, a group $S(O)_n$Alk, $OS(O)_n$Alk or $NR_7R_8$;

$R_6$ represents a hydrogen atom or a group $(C_1$-$C_4)$alkyl;

or $R_4$ and $R_6$, together with the nitrogen atom to which they are attached, constitute a heterocyclic radical of 3 to 8 atoms, possibly containing a second heteroatom chosen from an oxygen, sulfur or nitrogen atom, which is unsubstituted or substituted one or more times with identical or different substituents chosen from a group $(C_1$-$C_4)$alkyl, a group $(C_1$-$C_4)$alkanoyl, a group $NR_7R_8$ or $CONR_7R_8$, a phenyl group; the said phenyl group being unsubstituted or substituted one or more times with identical or different substituents chosen from a halogen atom, a group $(C_1$-$C_4)$alkyl, $(C_1$-$C_4)$alkoxy, trifluoromethyl, $(C_1$-$C_4)$alkylthio, trifluoromethoxy, trifluoromethylthio or a group $OS(O)_n$Alk, $S(O)_n$Alk or $NR_7R_8$;

$R_7$ and $R_8$ represent, independently of each other, a hydrogen atom, a group $(C_1$-$C_4)$alkyl or $R_7$ and $R_8$, together with the nitrogen atom to which they are attached, constitute a saturated heterocyclic radical of 4 to 8 atoms possibly containing another heteroatom chosen from a nitrogen, oxygen or sulfur atom;

$Ar_1$ and $Ar_2$ represent, independently of each other, a phenyl which is unsubstituted or substituted one or more times with identical or different substituents chosen from a halogen atom, a group $(C_1$-$C_6)$alkyl, $(C_1$-$C_6)$ alkoxy, $(C_1$-$C_6)$alkylthio, trifluoromethyl, trifluoromethoxy, trifluoromethylthio, cyano, nitro, a group $S(O)_n$Alk, $OS(O)_n$Alk or $NR_7R_8$;

Y represents a group —$R_{1'}$, —$OR_{5'}$, —$N(R_{3'})X'R_{4'}$, —$N(R_{3'}COOR_{5'}$, —$NR_7R_{8'}$, —$CON(R_{3'})R_{5'}$, —$CSN$ $(R_{3'})R_{5'}$, —$C(O)R_{2'}$, —$C(O)$—$O$—$R_{2'}$, —$SO_2R_{2'}$, —$SO_2N(R_{3'})R_5$ or —$OCON(R_3,R_{5'})$; $R_{1'}$ represents a radical —CN or a saturated or unsaturated, oxygen-bearing, sulfur-bearing or nitrogen-bearing heterocyclic radical of 3 to 8 atoms, possibly containing a second heteroatom chosen from nitrogen, oxygen and sulfur, which is unsubstituted or substituted with one or more identical or different substituents chosen from a halogen atom, a group $(C_1$-$C_4)$alkyl, hydroxyl, trifluoromethyl, $(C_1$-$C_4)$alkoxy, trifluoromethoxy, trifluoromethylthio, $(C_1$-$C_4)$alkylthio, cyano, nitro or with an oxo group;

X' represents a group —CO—, —$SO_2$—, —$CON(R_{6'})$— or —$CSN(R_{6'})$—;

$R_{2'}$ represents:

a group $(C_1$-$C_{10})$alkyl, which is unsubstituted or substituted with a substituent chosen from $CF_3$, $(C_1$-$C_4)$ alkoxy and hydroxyl;

a non-aromatic $(C_3$-$C_{12})$ carbocyclic radical, which is unsubstituted or substituted one or more times with identical or different substituents chosen from a halogen atom, a group $(C_1$-$C_4)$alkyl, hydroxyl, trifluoromethyl or $(C_1$-$C_4)$alkoxy, a phenyl which is unsubstituted or substituted one or more times with identical or different substituents chosen from a halogen atom, a group $(C_1$-$C_4)$alkyl, trifluoromethyl, trifluoromethoxy, cyano, nitro, ($C_1$-$C_4$)alkoxy, ($C_1$-$C_4$)alkylthio, trifluoromethylthio, $S(O)_n$Alk or $OS(O)_n$Alk;
- a benzyl which is unsubstituted or substituted one or more times with identical or different substituents chosen from a halogen atom, a group ($C_1$-$C_4$)alkyl, trifluoromethyl, trifluoromethoxy, cyano, nitro, ($C_1$-$C_4$)alkoxy, ($C_1$-$C_4$)alkylthio, trifluoromethylthio, $S(O)_n$Alk or $OS(O)_n$Alk;

$R_{3'}$ represents a hydrogen atom or a group ($C_1$-$C_4$)alkyl;

$R_{4'}$ represents:
- a group ($C_1$-$C_{10}$)alkyl, which is unsubstituted or substituted with a group $CF_3$;
- a non-aromatic ($C_3$-$C_{12}$) carbocyclic radical, which is unsubstituted or substituted one or more times with identical or different substituents chosen from a group ($C_1$-$C_4$)alkyl, hydroxyl, a halogen atom, a trifluoromethyl, ($C_1$-$C_4$)alkoxy, ($C_{1-4}$)alkylthio or cyano;
- a saturated or unsaturated, oxygen-bearing, sulfur-bearing or nitrogen-bearing heterocyclic radical of 3 to 8 atoms, which is unsubstituted or substituted with one or more identical or different substituents chosen from a halogen atom, a group ($C_1$-$C_4$)alkyl, hydroxyl, trifluoromethyl, ($C_1$-$C_4$)alkoxy, trifluoromethoxy, trifluoromethylthio, ($C_1$-$C_4$)alkylthio, cyano, nitro and an oxo group;
- an indolyl which is unsubstituted or substituted with a halogen atom, a group ($C_1$-$C_4$)alkyl, trifluoromethyl, hydroxyl, ($C_1$-$C_4$)alkoxy, trifluoromethoxy, trifluoromethylthio, ($C_1$-$C_4$)alkylthio, cyano or nitro;
- a tetrahydronaphthyl; a naphthyl;
- a benzothiophenyl or a benzofuryl;
- a phenyl which is unsubstituted or substituted one or more times with identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group $S(O)_n$Alk, $OS(O)_n$Alk or $NR_7R_8$;
- a benzodioxyl;
- a phenoxymethylene or a 1-phenoxyethylene, the phenyl groups being unsubstituted or substituted one or more times with identical or different substituents chosen from a halogen atom, a group ($C_1$-$C_4$)alkyl, trifluoromethyl, trifluoromethoxy, hydroxyl, ($C_1$-$C_4$) alkoxy, ($C_1$-$C_4$)alkylthio, trifluoromethylthio, cyano, nitro, ($C_1$-$C_4$)alkanoyl, phenyl or a group $S(O)_n$Alk, $OS(O)_n$Alk or $NR_7R_8$; the methylene or ethylene groups being unsubstituted or substituted one or more times with a group ($C_1$-$C_4$)alkyl or with a ($C_3$-$C_7$) cycloalkyl;
- a phenylcyclopropyl, the phenyl group being unsubstituted or substituted one or more times with identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group $S(O)_n$Alk, $OS(O)_n$Alk or $NR_7R_8$;
- a ($C_1$-$C_2$)alkylene substituted with one or two identical or different substituents chosen from:
  - (i) a $C_3$-$C_{12}$ non-aromatic carbocyclic radical which is unsubstituted or substituted one or more times with a group ($C_1$-$C_4$)alkyl;
  - (ii) a phenyl which is unsubstituted or substituted with one or more substituents, which may be identical or different, chosen from a halogen atom, a group ($C_1$-$C_4$)alkyl, hydroxyl, trifluoromethyl, ($C_1$-$C_4$) alkoxy, ($C_1$-$C_4$)alkylthio, trifluoromethoxy, trifluoromethylthio, ($C_1$-$C_4$)alkanoyl, cyano, nitro, phenyl or a group $S(O)_n$Alk, $OS(O)_n$Alk or $NR_7R_8$;
  - (iii) a saturated or unsaturated, oxygen-bearing, sulfur-bearing or nitrogen-bearing heterocyclic radical of 3 to 8 atoms, which is unsubstituted or substituted with one or more substituents, which may be identical or different, chosen from a halogen atom, a group ($C_1$-$C_4$)alkyl, hydroxyl, trifluoromethyl, ($C_1$-$C_4$)alkoxy, trifluoromethoxy, trifluoromethylthio, ($C_1$-$C_4$)alkylthio, cyano or nitro;
  furthermore, when X' represents a group —$CON(R_{6'})$— or —$CSN(R_{6'})$–, $R_{4'}$ may represent a group ($C_1$-$C_6$) alkanoyl or a benzoyl or benzylcarbonyl group, the phenyl group of the said groups being unsubstituted or substituted with identical or different substituents chosen from a halogen atom, a group ($C_1$-$C_4$)alkyl, trifluoromethyl, trifluoromethoxy, hydroxyl, ($C_1$-$C_4$) alkoxy, ($C_1$-$C_4$)alkylthio, trifluoromethylthio, cyano, nitro, ($C_1$-$C_4$)alkanoyl, phenyl or a group $S(O)_n$Alk, $OS(O)_n$Alk or $NR_7R_8$;

$R_{5'}$ represents:
- a hydrogen atom;
- a group ($C_1$-$C_{10}$)alkyl, which is unsubstituted or substituted with a group $CF_3$;
- a non-aromatic ($C_3$-$C_{12}$) carbocyclic radical, which is unsubstituted or substituted one or more times with identical or different substituents chosen from a halogen atom, a group ($C_1$-$C_4$)alkyl, hydroxyl, trifluoromethyl or ($C_1$-$C_4$)alkoxy;
- a phenyl which is unsubstituted or substituted one or more times with identical or different substituents chosen from a halogen atom, a group ($C_1$-$C_4$)alkyl, trifluoromethyl, trifluoromethoxy, cyano, nitro, ($C_1$-$C_4$)alkoxy, ($C_1$-$C_4$)alkylthio, trifluoromethylthio, $S(O)_n$Alk, $OS(O)_n$Alk or $NR_7R_8$, or $R_{3'}$ and $R_{5'}$, together with the nitrogen atom to which they are attached, constitute a heterocyclic radical of 3 to 8 atoms, possibly containing a second heteroatom chosen from an oxygen, sulfur or nitrogen atom, which is unsubstituted or substituted one or more times with identical or different substituents chosen from a halogen atom, a trifluoromethyl, a group ($C_1$-$C_4$)alkyl, a phenyl group or a group $NR_7R_8$, a group $CONR_7R_8$; the said group ($C_1$-$C_4$)alkyl being unsubstituted or substituted with a trifluoromethyl group; and the said phenyl group being unsubstituted or substituted one or more times with a halogen atom, a group ($C_1$-$C_4$)alkyl, ($C_1$-$C_4$) alkoxy, trifluoromethyl, ($C_1$-$C_4$)alkylthio, trifluoromethoxy, trifluoromethylthio, $OS(O)_n$Alk or $S(O)_n$-Alk;

$R_{6'}$ represents a hydrogen atom or a group ($C_1$-$C_4$)alkyl;

or $R_{4'}$ and $R_{6'}$, together with the nitrogen atom to which they are attached, constitute a heterocyclic radical of 3 to 8 atoms, possibly containing a second heteroatom chosen from an oxygen, sulfur or nitrogen atom, which is unsubstituted or substituted one or more times with identical or different substituents chosen from a group ($C_1$-$C_4$)alkyl, a phenyl group, a halogen atom, a hydroxyl, trifluoromethyl, ($C_1$-$C_4$)alkoxy, trifluoromethoxy, trifluoromethylthio, ($C_1$-$C_4$)alkylthio, an oxo group, ($C_1$-$C_4$)alkanoyl, $NR_7R_8$ or $CONR_7R_8$; the said group ($C_1$-$C_4$)alkyl being unsubstituted or substituted with a trifluoromethyl group; and the said phenyl group being unsubstituted or substituted one or more times with identical or different substituents chosen from a halogen atom, a group $(C_1-C_4)$alkyl, $(C_1-C_4)$alkoxy, trifluoromethyl, $(C_1-C_4)$alkylthio, trifluoromethoxy, trifluoromethylthio, $OS(O)_n$Alk or $S(O)_n$-Alk;

$R_{7'}$ and $R_{8'}$ represent, independently of each other, a hydrogen atom, a group $(C_1-C_4)$alkyl or $R_{7'}$ and $R_{8'}$, together with the nitrogen atom to which they are attached, constitute a saturated heterocyclic radical of 4 to 8 atoms possibly containing another heteroatom chosen from a nitrogen, oxygen or sulfur atom;

Alk represents a linear or branched $(C_1-C_7)$alkyl group;
Alk' represents a linear or branched $(C_1-C_5)$alkyl group;
n represents 0, 1 or 2;
k represents 0 or 1;
m represents 0 or 1;
in the form of base or of acid-addition salt.

Among the compounds of formula (I) that are subjects of the invention, the following are distinguished:
the compounds of formula (IA) in which Y represents a group —C(O)$R_{2'}$;
the compounds of formula (IB) in which Y represents a group —SO$_{2'}$, $R_{2'}$;
the compounds of formula (IC) in which Y represents a group —CON($R_{3'}$)$R_{5'}$;
the compounds of formula (ID) in which Y represents a group —CSN$R_{3'}R_{5'}$;
the compounds of formula (IE) in which Y represents a group —C(O)—O—$R_{2'}$;
the compounds of formula (IF) in which Y represents a group —NR$_{7'}$R$_{8'}$;
the compounds of formula (IH) in which Y represents a group —N($R_3$X'$R_{4'}$;
the compounds of formula (IJ) in which Y represents a group —O$R_{5'}$;
the compounds of formula (IK) in which Y represents a group —SO$_2$N($R_{3'}$)$R_{5'}$;
the compounds of formula (IL) in which Y represents a group —OCON ($R_{3'}$)$R_{5'}$;
the compounds of formula (IM) in which Y represents a group —$R_1$;
the compounds of formula (IN) in which Y represents a group —N($R_3$COO'$R_{5'}$.

According to a first variant of the invention, the compounds of formula (I) correspond to the following compounds:
the compounds of formula (IA$_1$) with Y representing a group —C(O)$R_{2'}$;
the compounds of formula (IB$_1$) with Y representing a group —SO$_2$R$_{2'}$;
the compounds of formula (IC$_1$) with Y representing a group —CON($R_{3'}$)$R_{5'}$;
the compounds of formula (ID$_1$) with Y representing a group —CSN$R_{3'}R_{5'}$;
the compounds of formula (IE$_1$) with Y representing a group —C(O)—O—$R_{2'}$;
the compounds of formula (IF$_1$) with Y representing a group —NR$_{7'}$R$_{8'}$;
the compounds of formula (IJ$_1$) in which Y represents a group —O$R_{5'}$;
the compounds of formula (IM$_1$) in which Y represents a group —$R_1$; in which k represents 1, Q represents the radical NR$_1$, R$_1$ preferably being a hydrogen atom or a methyl group, Alk' represents a linear (C$_2$-C$_4$)alkyl group, and the other substituents are as defined for the compounds of formula (I).

According to this first variant, $R_{2'}$, $R_{3'}$, $R_{5'}$, $R_{7'}$ and $R_{8'}$ preferably have the definitions hereinbelow.

$R_{2'}$ represents:
a group $(C_1-C_{10})$alkyl, which is unsubstituted or substituted with a substituent chosen from $CF_3$, $(C_1-C_4)$alkoxy and hydroxyl;
a non-aromatic $(C_3-C_{12})$ carbocyclic radical, which is unsubstituted or substituted one or more times with identical or different substituents chosen from a halogen atom, a group $(C_1-C_4)$alkyl, $(C_1-C_4)$alkoxy, hydroxyl and trifluoromethyl;
a phenyl which is unsubstituted or substituted one or more times with identical or different substituents chosen from a halogen atom, a group $(C_1-C_4)$alkyl, trifluoromethyl, trifluoromethoxy, $(C_1-C_4)$alkoxy, $(C_1-C_4)$alkylthio and trifluoromethylthio;
a benzyl which is unsubstituted or substituted one or more times with identical or different substituents chosen from a halogen atom, a group $(C_1-C_4)$alkyl, trifluoromethyl, trifluoromethoxy, $(C_1-C_4)$alkoxy, $(C_1-C_4)$alkylthio and trifluoromethylthio;

$R_{3'}$ represents a hydrogen atom or a group $(C_1-C_4)$alkyl;
$R_{5'}$ represents:
a hydrogen atom;
a group $(C_1-C_{10})$alkyl, which is unsubstituted or substituted with a group $CF_3$;
a non-aromatic $(C_3-C_{12})$ carbocyclic radical, which is unsubstituted or substituted one or more times with identical or different substituents chosen from a halogen atom, a group $(C_1-C_4)$alkyl, hydroxyl, trifluoromethyl, $(C_1-C_4)$alkoxy;
a phenyl which is unsubstituted or substituted one or more times with identical or different substituents chosen from a halogen atom, a group $(C_1-C_4)$alkyl, trifluoromethyl, trifluoromethoxy, $(C_1-C_4)$alkoxy, $(C_1-C_4)$alkylthio or trifluoromethylthio;

$R_{3'}$ and $R_{5'}$, together with the nitrogen atom to which they are attached, constitute a heterocyclic radical of 3 to 8 atoms, possibly containing a second heteroatom chosen from an oxygen, sulfur or nitrogen atom, which is unsubstituted or substituted one or more times with identical or different substituents chosen from a halogen atom, a trifluoromethyl or a group $(C_1-C_4)$alkyl, which is unsubstituted or substituted with a trifluoromethyl;

$R_{7'}$ and $R_{8'}$ represent, independently of each other, a hydrogen atom or a group $(C_1-C_4)$alkyl, or $R_{7'}$ and $R_{8'}$ together with the nitrogen atom to which they are attached, constitute a saturated heterocyclic radical of 4 to 8 atoms possibly containing another heteroatom chosen from a nitrogen, oxygen or sulfur atom.

According to this first variant, the compounds of formulae (IA$_1$), (IB$_1$), (IC$_1$) and (IJ$_1$) are particularly preferred.

According to a second variant of the invention, the compounds of formula (I) correspond to the following compounds:
the compounds of formula (IB$_2$) with Y representing a group —SO$_2$R$_{2'}$;
the compounds of formula (IC$_2$) with Y representing a group —CON($R_{3'}$)$R_{5'}$;
the compounds of formula (IF$_2$) with Y representing a group —NR$_{7'}$R$_{8'}$;
the compounds of formula (IJ$_2$) with Y representing a group —O$R_{5'}$;
the compounds of formula (IK$_2$) with Y representing a group —SO$_2$N($R_{3'}$)$R_{5'}$; in which k represents 1, Q represents an oxygen atom, Alk' represents a linear (C$_2$-C$_4$) alkyl group, and the other substituents are as defined for the compounds of formula (I).

According to this second variant, $R_{2'}$, $R_{3'}$, $R_{5'}$, $R_{7'}$ and $R_{8'}$ preferably have the definitions hereinbelow.

$R_{2'}$ represents:
- a group $(C_1-C_{10})$alkyl, which is unsubstituted or substituted with a substituent chosen from $CF_3$, $(C_1-C_4)$ alkoxy and hydroxyl;
- a $(C_3-C_{12})$ non-aromatic carbocyclic group, which is unsubstituted or substituted one or more times with identical or different substituents chosen from a halogen atom, a group $(C_1-C_4)$alkyl, hydroxyl, trifluoromethyl, $(C_1-C_4)$alkoxy;
- a phenyl which is unsubstituted or substituted one or more times with identical or different substituents chosen from a halogen atom, a group $(C_1-C_4)$alkyl, trifluoromethyl, trifluoromethoxy, $(C_1-C_4)$alkoxy, $(C_1-C_4)$alkylthio and trifluoromethylthio;

$R_{3'}$ represents a hydrogen atom or a group $(C_1-C_4)$alkyl:

$R_{5'}$ represents:
- a hydrogen atom;
- a group $(C_1-C_{10})$alkyl, which is unsubstituted or substituted with a group $CF_3$;
- a non-aromatic $(C_3-C_{12})$ carbocyclic radical, which is unsubstituted or substituted one or more times with identical or different substituents chosen from a halogen atom, a group $(C_1-C_4)$alkyl, hydroxyl, trifluoromethyl or $(C_1-C_4)$alkoxy;
- a phenyl which is unsubstituted or substituted one or more times with identical or different substituents chosen from a halogen atom, a group $(C_1-C_4)$alkyl, trifluoromethyl, trifluoromethoxy, $(C_1-C_4)$alkoxy, $(C_1-C_4)$alkylthio and trifluoromethylthio;

$R_{3'}$ and $R_{5'}$, together with the nitrogen atom to which they are attached, constitute a heterocyclic radical of 3 to 8 atoms, possibly containing a second heteroatom chosen from an oxygen, sulfur or nitrogen atom, which is unsubstituted or substituted one or more times with identical or different substituents chosen from a halogen atom, a trifluoromethyl or a group $(C_1-C_4)$alkyl, which is unsubstituted or substituted with a trifluoromethyl;

$R_{7'}$ and $R_{8'}$ represent, independently of each other, a hydrogen atom, a group $(C_1-C_4)$alkyl or $R_{7'}$ and $R_{8'}$, together with the nitrogen atom to which they are attached, constitute a saturated heterocyclic radical of 4 to 8 atoms possibly containing another heteroatom chosen from a nitrogen, oxygen or sulfur atom.

According to a third variant of the invention, the compounds of formula (I) correspond to the following compounds:
- the compounds of formula ($IA_3$) with Y representing a group —C(O)$R_{2'}$;
- the compounds of formula ($IB_3$) with Y representing a group —SO$_2R_{2'}$;
- the compounds of formula ($IC_3$) with Y representing a group —CON($R_{3'}$)$R_{5'}$;
- the compounds of formula ($IF_3$) with Y representing a group —N$R_{7'}R_{8'}$;
- the compounds of formula ($IH_3$) with Y representing a group —N($R_{3'}$X'$R_{4'}$;
- the compounds of formula ($IJ_3$) with Y representing a group —O$R_{5'}$;
- the compounds of formula ($IM_3$) with Y representing a group —$R_{1'}$;
- the compounds of formula ($IL_3$) with Y representing a group —OCON ($R_{3'}$)$R_{5'}$;

in which k represents 0, m represents 0 or 1, Q represents an oxygen atom, Alk' represents a linear $(C_2-C_4)$alkyl group, and the other substituents are as defined for the compounds of formula (I).

According to this third variant, $R_{1'}$, $R_{2'}$, $R_{3'}$, $R_{4'}$, $R_{5'}$, $R_{6'}$, $R_{7'}$, $R_{8'}$ and X' preferably have the definitions hereinbelow:

$R_{1'}$ represents an oxygen-bearing, sulfur-bearing or nitrogen-bearing, saturated or unsaturated, heterocyclic radical of 3 to 8 atoms, possibly containing a second heteroatom chosen from nitrogen, oxygen and sulfur, which is unsubstituted or substituted with one or more identical or different substituents chosen from a halogen atom, a group $(C_1-C_4)$alkyl, hydroxyl, trifluoromethyl, $(C_1-C_4)$alkoxy, trifluoromethoxy, trifluoromethylthio, $(C_1-C_4)$alkylthio or with an oxo group;

X' represents a group —CO—, —SO$_2$—, —CON($R_{6'}$)— or —CSN($R_{6'}$)—;

$R_{2'}$ represents:
- a group $(C_1-C_{10})$alkyl, which is unsubstituted or substituted with a substituent chosen from $CF_3$, $(C_1-C_4)$ alkoxy and hydroxyl;
- a non-aromatic $(C_3-C_{12})$ carbocyclic radical, which is unsubstituted or substituted one or more times with identical or different substituents chosen from a halogen atom, a group $(C_1-C_4)$alkyl, hydroxyl, trifluoromethyl or $(C_1-C_4)$alkoxy;
- a phenyl which is unsubstituted or substituted one or more times with identical or different substituents chosen from a halogen atom, a group $(C_1-C_4)$alkyl, trifluoromethyl, trifluoromethoxy, $(C_1-C_4)$alkoxy, $(C_1-C_4)$alkylthio and trifluoromethylthio;

$R_{3'}$ represents a hydrogen atom or a group $(C_1-C_4)$alkyl;

$R_{4'}$ represents:
- a group $(C_1-C_{10})$alkyl, which is unsubstituted or substituted with a group $CF_3$;
- a non-aromatic $(C_3-C_{12})$ carbocyclic radical, which is unsubstituted or substituted one or more times with identical or different substituents chosen from a group $(C_1-C_4)$alkyl, hydroxyl, a halogen atom, a trifluoromethyl or $(C_1-C_4)$alkoxy;
- a saturated or unsaturated, oxygen-bearing, sulfur-bearing or nitrogen-bearing heterocyclic radical of 3 to 8 atoms, which is unsubstituted or substituted with one or more identical or different substituents chosen from a halogen atom, a group $(C_1-C_4)$alkyl, hydroxyl, trifluoromethyl, $(C_1-C_4)$alkoxy, trifluoromethoxy, trifluoromethylthio, $(C_1-C_4)$alkylthio or an oxo group;
- a phenyl which is unsubstituted or substituted one or more times with identical or different substituents chosen from a halogen atom, a group $(C_1-C_4)$alkyl, trifluoromethyl, trifluoromethoxy, hydroxyl, $(C_1-C_4)$ alkoxy, $(C_1-C_4)$alkylthio, trifluoromethylthio or N$R_{7'}R_{8'}$;

$R_{5'}$ represents:
- a hydrogen atom;
- a group $(C_1-C_{10})$alkyl, which is unsubstituted or substituted with a group $CF_3$;
- a non-aromatic $(C_3-C_{12})$ carbocyclic radical, which is unsubstituted or substituted one or more times with identical or different substituents chosen from a halogen atom, a group $(C_1-C_4)$alkyl, hydroxyl, trifluoromethyl or $(C_1-C_4)$alkoxy;
- a phenyl which is unsubstituted or substituted one or more times with identical or different substituents chosen from a halogen atom, a group $(C_1-C_4)$alkyl, trifluoromethyl, trifluoromethoxy, ($C_1$-$C_4$)alkoxy, ($C_1$-$C_4$)alkylthio, trifluoromethylthio, $S(O)_n$Alk or $OS(O)_n$Alk;

$R_{3'}$ and $R_{5'}$, together with the nitrogen atom to which they are attached, constitute a heterocyclic radical of 3 to 8 atoms, possibly containing a second heteroatom chosen from an oxygen, sulfur or nitrogen atom, which is unsubstituted or substituted one or more times with identical or different substituents chosen from a halogen atom, a group ($C_1$-$C_4$)alkyl, a group $NR_{7'}R_{8'}$ or $CONR_{7'}R_{8'}$;

$R_{6'}$ represents a hydrogen atom or a group ($C_1$-$C_4$)alkyl;

or $R_{4'}$ and $R_{6'}$, together with the nitrogen atom to which they are attached, constitute a heterocyclic radical of 3 to 8 atoms, possibly containing a second heteroatom chosen from an oxygen, sulfur or nitrogen atom, which is unsubstituted or substituted one or more times with identical or different substituents chosen from a halogen atom, a hydroxyl, a trifluoromethyl, a ($C_1$-$C_4$)alkoxy, a trifluoromethoxy, a trifluoromethylthio, a ($C_1$-$C_4$)alkylthio, an oxo group or with a group ($C_1$-$C_4$)alkyl, which is unsubstituted or substituted with a trifluoromethyl group;

$R_{7'}$ and $R_{8'}$ represent, independently of each other, a hydrogen atom, a group ($C_1$-$C_4$)alkyl or $R_{7'}$ and $R_{8'}$, together with the nitrogen atom to which they are attached, constitute a saturated heterocyclic radical of 4 to 8 atoms possibly containing another heteroatom chosen from a nitrogen, oxygen or sulfur atom;

and Alk represents a linear or branched ($C_1$-$C_7$)alkyl group.

As regards Z within the compounds of formula (I), and in particular within the compounds of formulae corresponding to the three variants described above, the following three preferred groups Z are distinguished:

($Z_1$): —N($R_3$)COR$_4$;
($Z_2$): —N($R_3$)SO$_2$R$_4$;
and ($Z_3$): —N($R_3$)CON($R_6$)R$_4$;

in which $R_3$, $R_4$ and $R_6$ are as defined for the compounds of formula (I).

More particularly for these three preferred groups $Z_1$, $Z_2$ and $Z_3$:

$R_3$ represents a hydrogen atom or a group ($C_1$-$C_4$)alkyl;
$R_4$ represents:
- a group ($C_3$-$C_{10}$)alkyl;
- a non-aromatic ($C_3$-$C_{12}$) carbocyclic radical, which is unsubstituted or substituted one or more times with an identical or different ($C_1$-$C_4$)alkyl group;
- a saturated or unsaturated, oxygen-bearing, sulfur-bearing or nitrogen-bearing heterocyclic radical of 4 to 8 atoms, which is unsubstituted or substituted with one or more identical or different substituents chosen from a halogen atom, a group ($C_1$-$C_4$)alkyl, hydroxyl, trifluoromethyl, ($C_1$-$C_4$)alkoxy, trifluoromethoxy, ($C_1$-$C_4$)alkylthio, cyano or nitro;
- an indolyl which is unsubstituted or substituted on the nitrogen atom with a halogen atom, a group ($C_1$-$C_4$)alkyl or a group ($C_1$-$C_4$)alkoxy;
- a phenyl which is unsubstituted or substituted one or more times with identical or different substituents chosen from a halogen atom, a group ($C_1$-$C_4$)alkyl, trifluoromethyl, trifluoromethoxy, ($C_1$-$C_4$)alkoxy, ($C_1$-$C_4$)alkylthio, trifluoromethylthio, cyano, ($C_1$-$C_4$) alkanoyl, phenyl or a group $S(O)_n$Alk or $OS(O)_n$Alk;
- a benzyl which is unsubstituted or substituted one or more times with identical or different substituents chosen from a halogen atom, a group ($C_1$-$C_4$)alkyl, trifluoromethyl, trifluoromethoxy, trifluoromethylthio, ($C_1$-$C_4$)alkoxy, cyano, phenyl or a group $S(O)_n$Alk or $OS(O)_n$Alk;

$R_6$ represents a hydrogen atom or a group ($C_1$-$C_4$)alkyl;

or $R_4$ and $R_6$, together with the nitrogen atom to which they are attached, constituent a heterocyclic radical of 4 to 8 atoms, possibly containing a second heteroatom chosen from an oxygen, sulfur or nitrogen atom, which is unsubstituted or substituted one or more times with identical or different substituents chosen from a group ($C_1$-$C_4$)alkyl, a group ($C_1$-$C_4$)alkanoyl, a group $NR_7R_8$ or $CONR_7R_8$, a phenyl group; the said phenyl group being unsubstituted or substituted one or more times with identical or different substituents chosen from a halogen atom, a group ($C_1$-$C_4$)alkyl, ($C_1$-$C_4$)alkoxy or trifluoromethyl;

$R_7$ and $R_8$ represent, independently of each other, a hydrogen atom, a group ($C_1$-$C_4$)alkyl or $R_7$ and $R_8$, together with the nitrogen atom to which they are attached, constitute a heterocyclic radical chosen from piperidyl, pyrrolidinyl, piperazinyl, N-methylpiperazinyl, azepinyl and morpholinyl;

n represents 0, 1 or 2;

and Alk represents a linear or branched ($C_1$-$C_7$)alkyl group.

In particular, the definitions of the substituents for $Z_1$ et $Z_2$ are the following:

$R_3$ represents a hydrogen atom or a methyl, preferably a hydrogen atom;
$R_4$ represents:
- a ($C_5$-$C_{10}$)alkyl;
- a ($C_5$-$C_7$)cycloalkyl which is unsubstituted or substituted one or more times with a methyl;
- a saturated oxygen-bearing, sulfur-bearing or nitrogen-bearing heterocyclic radical of 4 to 8 atoms, which is unsubstituted or substituted one or more times with a methyl;
- a phenyl substituted one or more times with a halogen atom or groups chosen independently from a trifluoromethyl, trifluoromethoxy, trifluoromethylthio, ($C_1$-$C_4$)alkoxy, ($C_1$-$C_4$)alkylthio, SO$_2$Alk or OSO$_2$Alk group, and Alk represents a linear or branched ($C_1$-$C_7$)alkyl group.

Even more particularly for $Z_1$ and for $Z_2$, $R_4$ represents a 2-propylpentyl, 1-propylbutyl, 5-methylnonyl, 4-methylheptyl or 4-methyl-2,6-dimethylheptyl group, a cyclopentyl, tetramethylcyclopentyl, cyclohexyl, tetrahydrofuranyl, pyrrolidinyl, 1,1,4,4-tetramethylcyclopentyl, 2,2,5,5-tetramethylfuranyl or 2,2,5,5-tetramethylpyrrolidinyl group, a phenyl group which is unsubstituted or substituted with a halogen atom, a trifluoromethyl, a trifluoromethoxy, a trifluoromethylthio or with a group SO$_2$Alk or OSO$_2$Alk. Alk represents a linear or branched ($C_1$-$C_7$)alkyl group.

In particular, the definitions of the substituents for $Z_3$ are the following:

$R_3$ represents a hydrogen atom or a methyl;
$R_4$ represents:
- a ($C_5$-$C_{10}$)alkyl;
- a ($C_5$-$C_7$)cycloalkyl which is unsubstituted or substituted one or more times with a methyl;
- a saturated oxygen-bearing, sulfur-bearing or nitrogen-bearing heterocyclic radical of 4 to 8 atoms, which is unsubstituted or substituted one or more times with a methyl;
- a phenyl substituted one or more times with groups chosen independently from a halogen atom, a trifluoromethyl group, trifluoromethoxy, trifluoromethylthio, $(C_1-C_4)$alkoxy, $(C_1-C_4)$alkylthio, $SO_2Alk$ or $OSO_2Alk$;

Alk represents a linear or branched $(C_1-C_7)$alkyl group;

and $R_6$ represents a hydrogen atom or a methyl.

Even more particularly for $Z_3$, $R_4$ represents a cyclohexyl group, a phenyl group which is unsubstituted or substituted with a halogen atom or with a methoxy, trifluoromethyl, trifluoromethoxy or trifluoromethylthio group.

For the groups $Ar_1$ and $Ar_2$, the latter preferably represent, independently of each other, a phenyl which is unsubstituted or substituted one or more times with substituents each independently chosen from a chlorine or bromine atom and a methoxy or methylthio group. More preferentially, $Ar_1$ represents a phenyl substituted with a chlorine or bromine atom, and $Ar_2$ represents a phenyl substituted with at least two halogen atoms; the two identical or different halogen atoms being chosen from chlorine or bromine.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts may be prepared with pharmaceutically acceptable acids, but the salts of other acids that are useful, for example, for purifying or isolating the compounds of formula (I) also form part of the invention.

In the context of the present invention, the following definitions apply:

a halogen atom: a fluorine, a chlorine, a bromine or an iodine;

a group $(C_1-C_4)$alkyl or, respectively, $(C_2-C_6)$alkyl, $(C_1-C_6)$alkyl, $(C_2-C_4)$alkyl, $(C_1-C_5)$alkyl, $(C_1-C_7)$alkyl, $(C_1-C_{10})$alkyl, $(C_5-C_{10})$alkyl: a linear or branched saturated aliphatic group, of $(C_1-C_4)$, or, respectively, of $(C_2-C_6)$, $(C_1-C_6)$, $(C_2-C_4)$, $(C_1-C_5)$, $(C_1-C_7)$, $(C_1-C_{10})$ or $(C_5-C_{10})$. Examples that may be mentioned include methyl, ethyl, propyl, isopropyl, butyl, isobutyl, tert-butyl, pentyl, hexyl, 1-ethylpropyl, 1-propylbutyl, 2-propylpentyl, 5-methylnonyl, 4-methylheptyl, 4-methyl-2,6-dimethylheptyl etc. groups;

a group $(C_1-C_4)$alkoxy or, respectively, $(C_1-C_6)$alkoxy: a radical O-alkyl in which the alkyl group is as defined previously;

a group $(C_1-C_4)$alkylthio; a radical S-alkyl in which the alkyl group is as defined previously;

a group $(C_1-C_4)$alkanoyl; an alkylcarbonyl radical in which the alkyl group is as defined previously.

The non-aromatic $C_3-C_{12}$ carbocyclic radicals comprise fused or bridged monocyclic or polycyclic radicals. The monocyclic radicals include, for example, cycloalkyls, for example cyclopropyl, cyclobutyl, cyclopentyl, cyclohexyl, cycloheptyl or cyclooctyl; cyclohexyl and cyclopentyl being preferred. The fused, bridged or spirane bicyclic or tricyclic radicals include, for example, norbornyl, bornyl, isobornyl, noradamantyl, adamantyl, spiro[5.5]undecanyl, bicyclo[2.2.1]heptyl, bicyclo[3.2.1]octyl; bicyclo[3.1.1]heptyl.

The 3- to 8-membered nitrogen-bearing heterocyclic radicals constituted by two substituents, together with the nitrogen atom to which they are attached, comprise saturated radicals such as aziridinyl, azetidinyl, pyrrolidinyl, piperidyl, perhydroazepinyl, perhydroazocinyl; saturated or unsaturated radicals also containing a second heteroatom chosen from an oxygen, sulfur or nitrogen atom, such as imidazolidinyl, pyrazolidinyl, piperazinyl, morpholinyl, thiomorpholinyl, imidazolyl, pyrazolyl, isothiazolyl, isoxazolyl, triazolyl, tetrazolyl, oxazolyl or thiazolyl. The unsaturated 3- to 8-membered nitrogen-bearing heterocyclic radicals also comprising one or more heteroatoms comprise imidazolyl, pyrrolyl, pyrazolyl, isothiazolyl and isoxazolyl.

The saturated or unsaturated, oxygen-bearing, sulfur-bearing or nitrogen-bearing heterocyclic radicals of 3 to 8 atoms in particular comprise furyl, tetrahydrofuryl, thienyl and pyrrolyl.

Among the compounds according to the invention, mention may be made especially of the following compounds:

N-{[6-(4-bromophenyl)-2-[(butyrylamino)methyl]-5-(2,4-dichlorophenyl)pyrid-3-yl]methyl}-4-[(trifluoromethyl)thio]benzamide;

N-{[6-(4-bromophenyl)-5-(2,4-dichlorophenyl)-2-{[(methoxyacetyl)amino]-methyl}pyrid-3-yl]methyl}-4-[(trifluoromethyl)thio]benzamide;

N-({6-(4-bromophenyl)-5-(2,4-dichlorophenyl)-2-[(hydroxyacetylamino)methyl]pyrid-3-yl}methyl)-4-[(trifluoromethyl)thio]benzamide;

N-{[6-(4-bromophenyl)-5-(2,4-dichlorophenyl)-2-{[(propylsulfonyl)amino]-methyl}pyrid-3-yl]methyl}-4-(trifluoromethyl)benzamide;

N-({6-(4-bromophenyl)-5-(2,4-dichlorophenyl)-2-[({[4-(trifluoromethyl)-phenyl]sulfonyl}amino)methyl]pyrid-3-yl}methyl)-4-(trifluoromethyl)benzamide;

N-({6-(4-bromophenyl)-5-(2,4-dichlorophenyl)-2-[({[4-(trifluoromethyl)-benzyl]sulfonyl}amino)methyl]pyrid-3-yl}methyl)-4-(trifluoromethyl)benzamide;

N-{[6-(4-bromophenyl)-5-(2,4-dichlorophenyl)-2-{[(methylsulfonyl)amino]-methyl}pyrid-3-yl]methyl}-4-[(trifluoromethyl)thio]benzamide;

N-{[6-(4-bromophenyl)-5-(2,4-dichlorophenyl)-2-{[(propylcarbamoyl)amino]-methyl}pyrid-3-yl]methyl}-4-[(trifluoromethyl)thio]benzamide;

N-{[2-{[(anilinocarbonyl)amino]methyl}-6-(4-bromophenyl)-5-(2,4-dichloro-phenyl)pyrid-3-yl]methyl}-4-[(trifluoromethyl)thio]benzamide;

N-{[6-(4-bromophenyl)-5-(2,4-dichlorophenyl)-2-({[(propylamino)-carbonothioyl]amino}methyl)pyrid-3-yl]methyl}-4-(trifluoromethyl)benzamide;

propyl({6-(4-bromophenyl)-5-(2,4-dichlorophenyl)-3-[({4-[(trifluoromethyl)-thio]benzoyl}amino)methyl]pyrid-2-yl}methyl)carbamate;

N-{[6-(4-bromophenyl)-5-(2,4-dichlorophenyl)-2-({[2-(dimethylamino)-ethyl]amino}methyl)pyrid-3-yl]methyl}-4-[(trifluoromethyl)thio]benzamide;

N-{[6-(4-bromophenyl)-5-(2,4-dichlorophenyl)-2-{[(2-hydroxyethyl)(methyl)-amino]methyl}pyrid-3-yl]methyl}-4-(trifluoromethyl)benzamide;

N-{[2-{[(3-amino-3-oxoethyl)(methyl)amino]-methyl]-6-(4-bromophenyl)-5-(2,4-dichlorophenyl)pyrid-3-yl]methyl}-4-(trifluoromethyl)benzamide;

N-{[6-(4-bromophenyl)-5-(2,4-dichlorophenyl)-2-({methyl[2-(methylsulfonyl)-ethyl]amino}methyl)pyrid-3-yl]methyl}-4-(trifluoromethyl)benzamide;

N-{[6-(4-chlorophenyl)-5-(2,4-dichlorophenyl)-2-{[(hydroxyacetyl)amino]-methyl}pyrid-3-yl]methyl}-4-[(trifluoromethyl)thio]benzamide;

N-{[6-(4-chlorophenyl)-5-(2,4-dichlorophenyl)-3-({[(2-fluorobenzyl)carbamoyl]amino}methyl)pyrid-2-yl]methyl}-2-hydroxyacetamide;

N-{[6-(4-chlorophenyl)-5-(2,4-dichlorophenyl)-2-{[(hydroxyacetyl)amino]methyl}pyrid-3-yl]methyl}-4-(trifluoromethyl)benzamide;

N-{[6-(4-chlorophenyl)-5-(2,4-dichlorophenyl)-2-{[(3-hydroxypropanoyl)amino]methyl}pyrid-3-yl]methyl}-4-(trifluoromethyl)benzamide;

N-{[6-(4-bromophenyl)-5-(2,4-dichlorophenyl)-2-({[2-(dimethylamino)-ethyl]amino}methyl)pyrid-3-yl]methyl}-4-[(trifluoromethyl)thio]benzamide;

N-{[6-(4-bromophenyl)-5-(2,4-dichlorophenyl)-2-{[2-(dimethylamino)-ethoxy]methyl}pyrid-3-yl]methyl}-4-[(trifluoromethyl)thio]benzamide;

[6-(4-bromophenyl)-5-(2,4-dichlorophenyl)-3-({[4-(trifluoromethyl)-benzoyl]amino}methyl)pyrid-2-yl]methyl propylcarbamate;

N-{[6-(4-chlorophenyl)-5-(2,4-dichlorophenyl)-2-{2-[(methylsulfonyl)amino]-ethoxy}pyrid-3-yl]methyl}-4-(trifluoromethyl)benzamide;

N-{[6-(4-chlorophenyl)-5-(2,4-dichlorophenyl)-2-{3-[(methylsulfonyl)amino]-propoxy}pyrid-3-yl]methyl}-4-(trifluoromethyl)benzamide;

N-{[6-(4-chlorophenyl)-5-(2,4-dichlorophenyl)-2-{2-[(isopropylsulfonyl)-amino]ethoxy}pyrid-3-yl]methyl}-4-(trifluoromethyl)benzamide;

N-{[6-(4-chlorophenyl)-5-(2,4-dichlorophenyl)-2-{2-[(methylsulfonyl)amino]-ethoxy}pyrid-3-yl]methyl}-4-[(trifluoromethyl)thio]benzamide;

N-{[2-(2-aminoethoxy)-6-(4-chlorophenyl)-5-(2,4-dichlorophenyl)pyrid-3-yl]methyl}-4-(trifluoromethyl)benzamide;

N-{[6-(4-chlorophenyl)-2-{2-[(cyclopropylcarbonyl)amino]ethoxy}-5-(2,4-dichlorophenyl)pyrid-3-yl]methyl}-4-(trifluoromethyl)benzamide;

in the form of bases or of acid-addition salts.

Among these compounds, the following compounds are preferred:

N-{[6-(4-bromophenyl)-5-(2,4-dichlorophenyl)-2-{[(hydroxyacetyl)amino]-methyl}pyrid-3-yl]methyl}-4-[(trifluoromethyl)thio]benzamide;

N-{[6-(4-bromophenyl)-5-(2,4-dichlorophenyl)-2-{[(2-hydroxyethyl)(methyl)-amino]methyl}pyrid-3-yl]methyl}-4-(trifluoromethyl)benzamide;

N-{[2-{[(3-amino-3-oxopropyl)(methyl)amino]methyl}-6-(4-bromophenyl)-5-(2,4-dichlorophenyl)pyrid-3-yl]methyl}-4-(trifluoromethyl)benzamide;

N-{[6-(4-bromophenyl)-5-(2,4-dichlorophenyl)-2-({methyl[2-(methylsulfonyl)-ethyl]amino}methyl)pyrid-3-yl]methyl}-4-(trifluoromethyl)benzamide;

N-{[6-(4-chlorophenyl)-5-(2,4-dichlorophenyl)-2-{[(hydroxyacetyl)-amino]methyl}pyrid-3-yl]methyl}-4-[(trifluoromethyl)thio]benzamide;

N-{[6-(4-chlorophenyl)-5-(2,4-dichlorophenyl)-3-({[(2-fluorobenzyl)carbamoyl]amino}methyl)pyrid-2-yl]methyl}-2-hydroxyacetamide;

N-{[6-(4-chlorophenyl)-5-(2,4-dichlorophenyl)-2-{[(hydroxyacetyl)amino]-methyl}pyrid-3-yl]methyl}-4-(trifluoromethyl)benzamide;

N-{[6-(4-chlorophenyl)-5-(2,4-dichlorophenyl)-2-{[(3-hydroxypropanoyl)-amino]methyl}pyrid-3-yl]methyl}-4-(trifluoromethyl)benzamide; in the form of bases or of acid-addition salts.

More particularly, the following compounds are preferred:

N-{[6-(4-bromophenyl)-5-(2,4-dichlorophenyl)-2-{[(hydroxyacetyl)amino]-methyl}pyrid-3-yl]methyl}-4-[(trifluoromethyl)thio]benzamide;

N-{[6-(4-chlorophenyl)-5-(2,4-dichlorophenyl)-2-{[(hydroxyacetyl)amino]methyl}pyrid-3-yl]methyl}-4-[(trifluoromethyl)thio]benzamide;

N-{[6-(4-chlorophenyl)-5-(2,4-dichlorophenyl)-3-({[(2-fluorobenzyl)carbamoyl]amino}methyl)pyrid-2-yl]methyl}-2-hydroxyacetamide;

N-{[6-(4-chlorophenyl)-5-(2,4-dichlorophenyl)-2-{[(hydroxyacetyl)amino]methyl}pyrid-3-yl]methyl}-4-(trifluoromethyl)benzamide;

in the form of bases or of acid-addition salts.

In accordance with the invention, a compound of general formula (II) in which Z, $Ar_1$ and $Ar_2$ are as defined for (I):

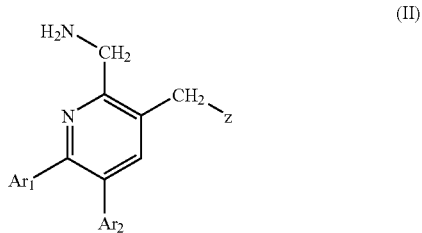

is treated either with an acid (III) of general formula $R_2 \cdot CO_2H$ in which $R_{2'}$ is as defined in (I) or with an activated derivative of the said acid to obtain a compound of general formula ($IA_1$):

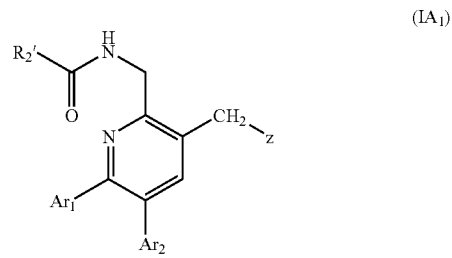

or with a sulfonyl halide (IV) of general formula $R_{2'}SO_2Hal$ in which $R_{2'}$ is as defined in (I) and Hal represents a halogen, preferentially chlorine, to obtain a compound of general formula ($IB_1$):

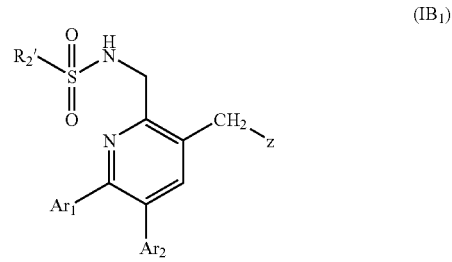

or with an isocyanate (V) of general formula $R_{5'}$—N═C═O in which $R_{5'}$ is as defined in (I), to obtain a compound of general formula ($IC_1$) in which $R_{3'}$ corresponds to a hydrogen atom:

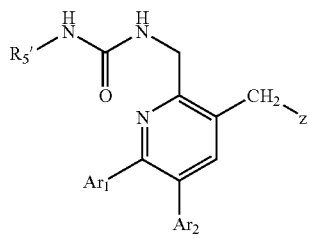

(IC₁)

or with an isothiocyanate (Vbis) of general formula $R_{5'}$—N=C=S in which $R_{5'}$ is as defined in (I), to obtain a compound of general formula (ID₁):

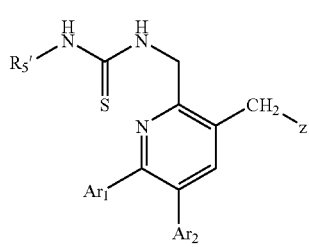

(ID₁)

or with an aryloxycarbonyl halide (VI) of general formula Hal COOR₂, in which $R_{2'}$ is as defined in (I) and Hal represents a halogen, to obtain a compound of general formula (IE₁):

(IE₁)

Alternatively, according to the invention, a compound (IE₁) as defined above may be considered as an intermediate for obtaining other compounds (I) according to the invention. In particular, (IE₁) is treated with an amine (VII) of general formula $R_{3'}R_{5'}NH$ in which $R_{3'}$ and $R_{5'}$ are as defined in (I) when a compound of general formula (IC₁) is to be prepared:

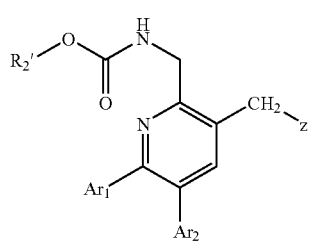

(IC₁)

In accordance with the invention, the compounds of general formula (IF₁), (IJ₁) or (IM₁) are prepared according to the following reaction scheme:

SCHEME 1

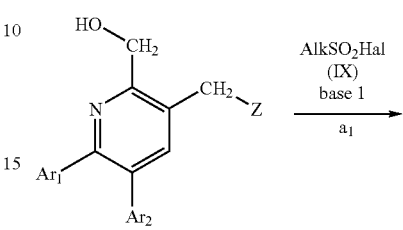

In step a₁, an alcohol of general formula (VIII) is treated with a sulfonyl halide (IX) of general formula Alk-SO₂-Hal in which Alk represents an alkyl radical, preferably methyl, and Hal a halogen, preferably chlorine, for instance methanesulfonyl chloride in the presence of a base, preferably triethylamine, to give a compound of general formula (X).

This compound (X) comprising a leaving group is treated with a primary amine (XI) of general formula Y-(Alk')ₘ—NH₂ in which Y, Alk' and m correspond to the definitions given for formulae (IF₁), (IJ₁) and (IM₁), in the presence of a base, for instance potassium carbonate.

In accordance with the invention, the compound of general formula (X) also gives access to a compound of general formula (IF₂) when it is treated with an alcohol (XII) of general formula $R_{7'}R_{8'}N$-(Alk')ₘ—OH in which $R_{7'}$ and $R_{8'}$, Alk' and m are as defined in (I), in the presence of a base, for instance potassium tert-butoxide in an aprotic solvent such as dioxane at high temperature:

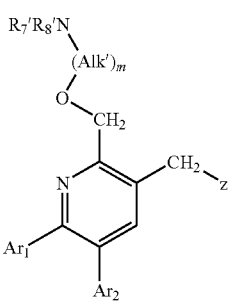

(IF₂)

According to the invention, when a compound of general formula (VIII) is treated with an isocyanate (V) of general formula $R_{5'}$—N═C═O in which $R_{5'}$ is defined for (I), a carbamate of general formula (IC₂) is obtained:

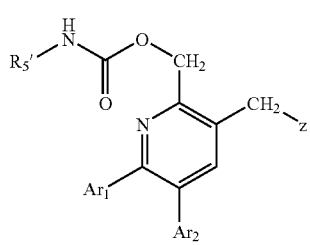

(IC₂)

When Z═—N(R₃)XR₄ or —N(R₃)COOR₅ with X═—CO, —SO₂, —CONR₆ or —CSNR₆ with R₃, R₄, R₅ and R₆ as defined in (I), the compound of general formula (VIII) is obtained according to the reaction scheme below:

SCHEME 2

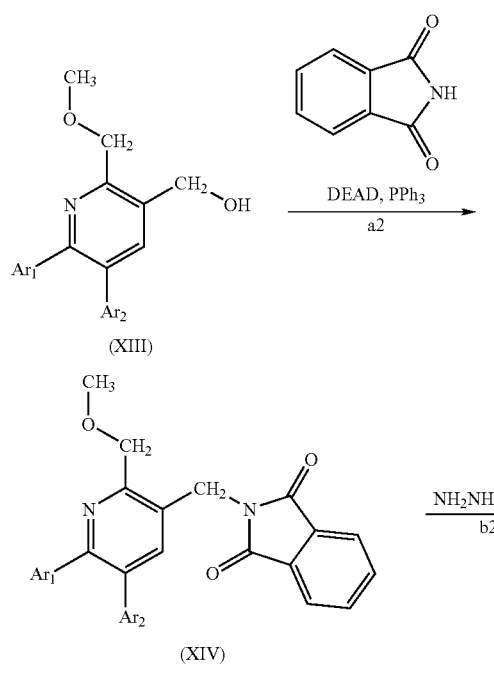

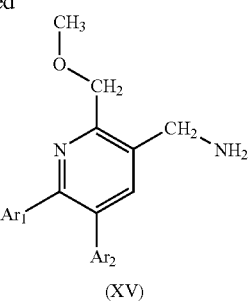

(XV)

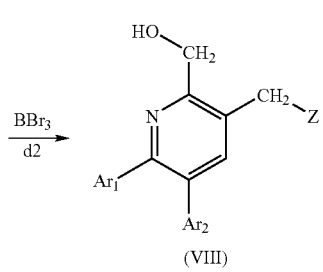

In step a₂, the compound of general formula (XIII) bearing a hydroxyl group is used in a Mitsunobu reaction in the presence of phthalimide, DEAD and triphenylphosphine to give a compound of general formula (XIV), which, when treated in step b₂ with hydrazine hydrate in refluxing methanol, gives an amine of general formula (XV).

This amine of formula (XV) is a key intermediate, and affords access in step c₂ to different variations of Z according to the processes described in patent application WO 2006/042 955 A1. In particular, the amine of formula (XV) is reacted with one of the following reagents: R₄—CO₂H, R₄SO₂Cl, R₄N═C═O, R₄—N═C═S, Hal-COOR₅.

The compounds of general formula (XVI) thus obtained are treated in step d₂ with a dealkylating agent, for instance boron tribromide or hydrobromic acid, to give the compound of general formula (VIII).

The compounds of general formula (II) are obtained from the compound of general formula (VIII) according to the following reaction scheme:

SCHEME 3

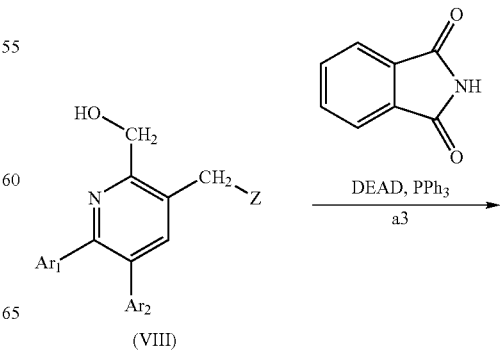

-continued

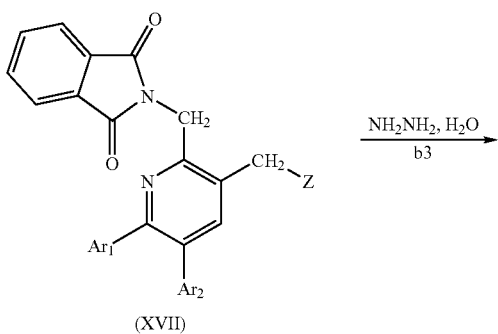

(XVII)

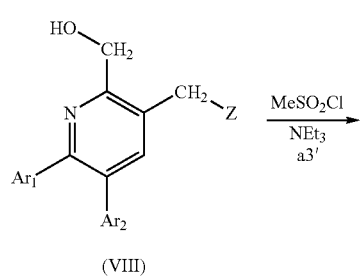

(II)

In step $a_3$, the compound of general formula (VIII) is used in a Mitsunobu reaction in the presence of phthalimide, DEAD and $PPh_3$ to give an intermediate (XVII), which, after treatment with hydrazine hydrate in step $b_3$, gives the compound of general formula (II).

Alternatively, the compounds of formula (II) may be obtained from a compound of general formula (VIII) according to the following reaction scheme.

SCHEME 3'

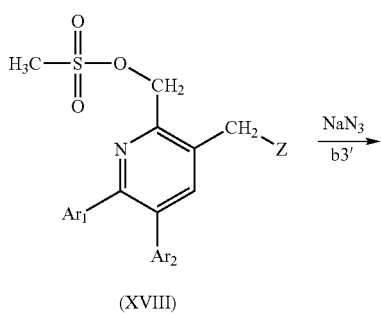

(VIII)

-continued

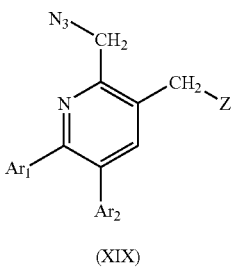

(XIX)

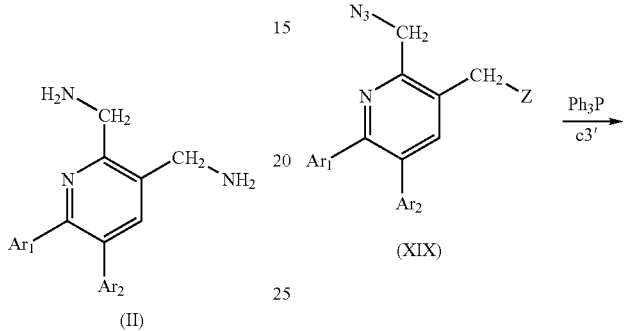

(XIX)

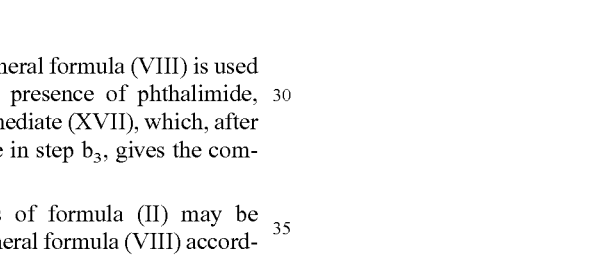

(II)

In step a3', a leaving group is introduced onto the alcohol function, for example an alkylsulfonate such as methanesulfonate. The compounds of general formula (XVIII) thus obtained may be used in a substitution reaction in the presence of sodium azide to give the azides of general formula (XIX). These azides may be reduced in the presence, for example, of triphenylphosphine to give the amines of general formula (II).

The preparation of the compound of general formula (XIII) is described in patent application WO 2006/042 955 A1.

According to the invention, when a compound of general formula (XX) in which $Ar_1$, $Ar_2$ and Z are as defined for (I) is treated with an alkylating agent (XXI) of general formula N-phthalimide-(Alk')$_m$-Hal in which Alk' and m are as defined for (I) and Hal represents a leaving group, for instance a halogen atom, preferably bromine, in the presence of a base, for instance potassium carbonate, cesium carbonate or silver carbonate, in a solvent, for instance toluene or chloroform, at the reflux temperature of these solvents, the compound of general formula (XXII) is obtained. In this reaction, the alkylating agent (XXI) may bear an amine-function protecting group other than the phthalimido group, for instance the BOC group.

According to step $b_4$ of the reaction scheme 4, when a compound (XXII) is treated with hydrazine hydrate in refluxing methanol, a compound of general formula (IF$_3$) for which the groups $R_{7'}$ and $R_{8'}$ are both hydrogen atoms, is obtained:

SCHEME 4
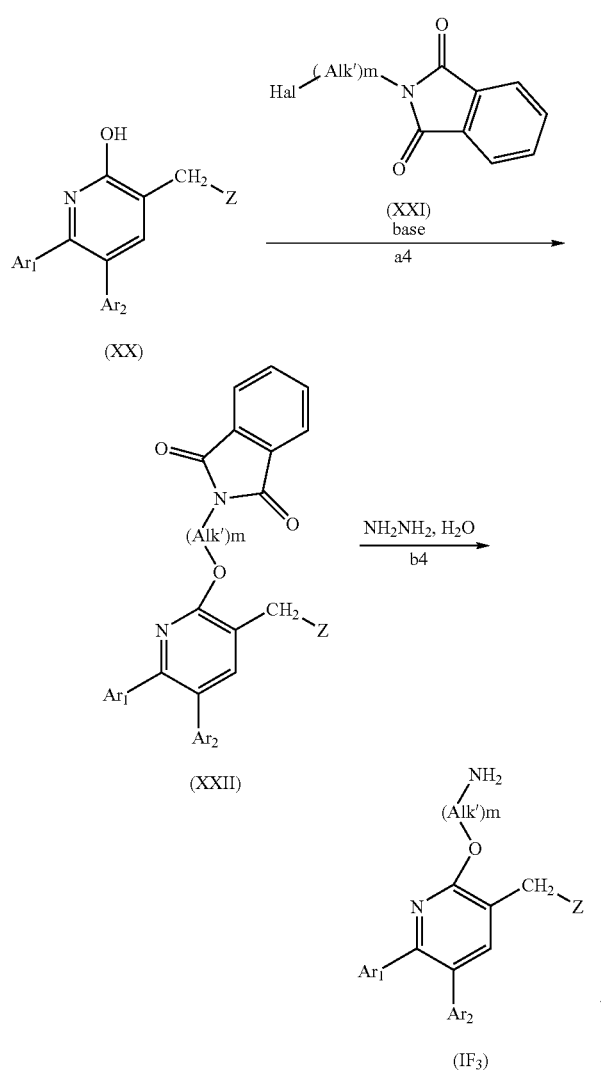
Such a compound IF$_3$, in addition to being a compound (I) according to the invention, is also an intermediate allowing access, for example, to different compounds of general formula (IH$_3$):
SCHEME 5
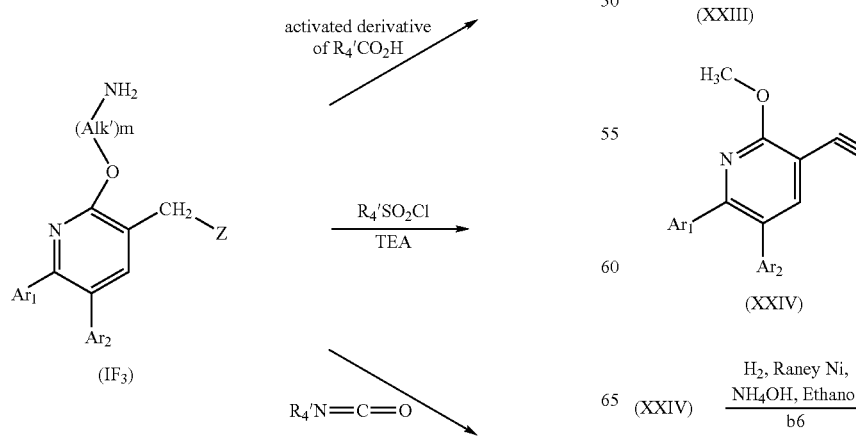
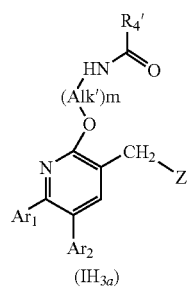
(IH$_{3a}$)
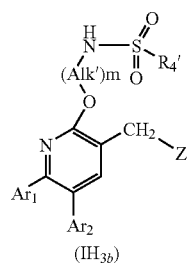
(IH$_{3b}$)
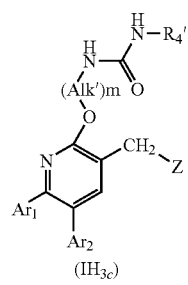
(IH$_{3c}$)
Scheme 6 below illustrates the method for preparing the compounds of general formula (XX):
SCHEME 6
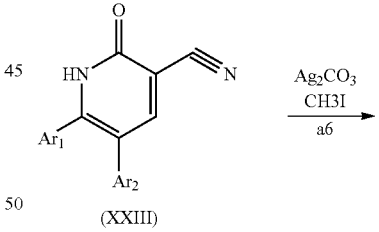

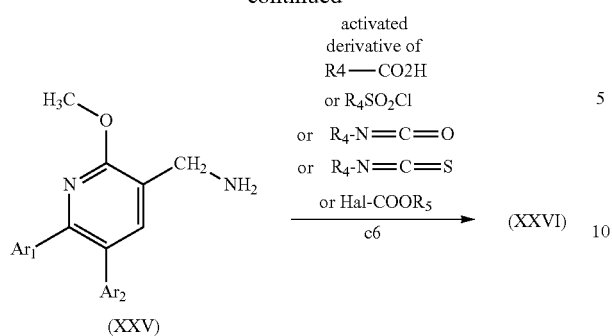

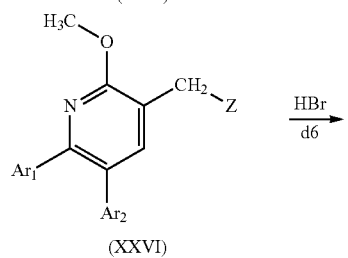

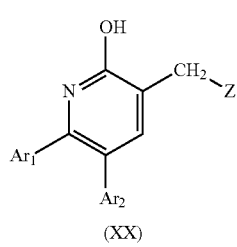

In step $a_6$, the pyridone (XXIII) is O-alkylated using methyl iodide in the presence of a base such as silver carbonate, to give the pyridine of general formula (XXIV).

The reaction also furnishes the N-methylpyridone of general formula (XXIVbis), which is separated from the desired compound of general formula (XXIV) via chromatographic methods or by recrystallization.

In step $b_6$, the nitrile function present on the compound of general formula (XXIV) is reduced to a primary amine function to give a compound of general formula (XXV). This reduction is performed, for example, either by catalytic hydrogenation in the presence of Raney nickel and aqueous ammonia, or using the borane-dimethyl sulfide complex.

The amine of general formula (XXV), which is a key intermediate, affords access in step c6 to different variations of Z defined for (I) according to the processes described in patent application WO 2006/042 955 A1. In accordance with scheme 6, the compounds of formula (XXVI) in which Z corresponds to —NH—SO2-$R_4$, —NH—CO$R_4$, —NH—CO—NH$R_4$ or —NH—CS—NH$R_4$ are especially obtained.

Finally, in step $d_6$, the compounds of general formula (XXVI) obtained in the preceding step are treated with a dealkylating agent to give the compounds of general formula (XX). Various types of dealkylating agent may be used; for example, hydrobromic acid or boron tribromide.

Patent application WO 2003/082 191 describes the preparation for arriving at the compounds of general formula (XXIII) and also the chlorinated compounds of general formula (XXVII):

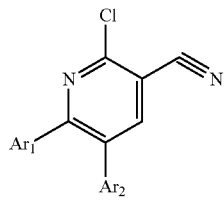

This compound of general formula (XXVII) is very useful for preparing the compounds of general formula (IF$_4$) according to Scheme 7 below.

For the compounds (IF$_4$), Y corresponds to —NR$_7$R$_{8'}$—, Q corresponds to NH, Alk' corresponds to a linear or branched ($C_1$-$C_5$)alkyl group, k is equal to zero, and m is equal to 1.

SCHEME 7

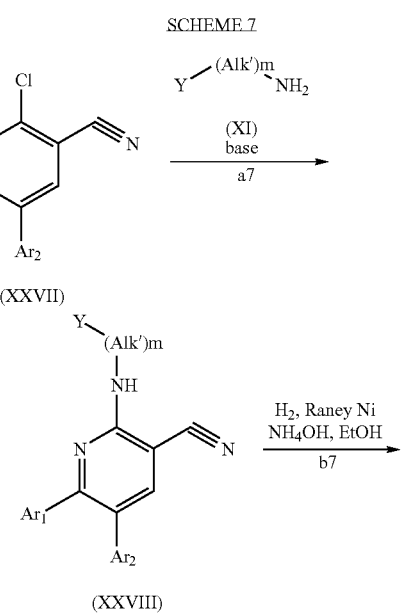

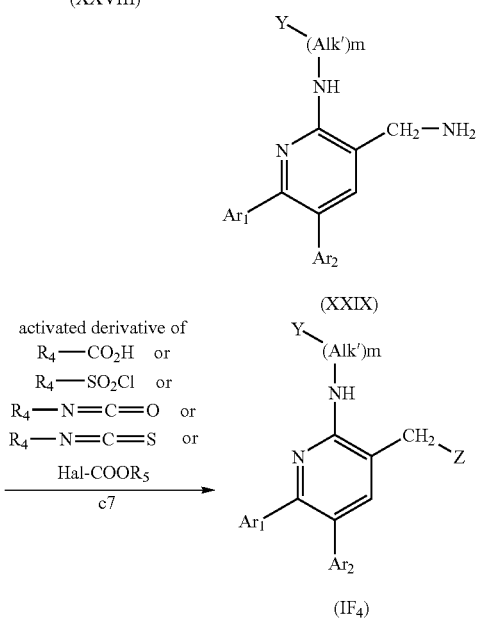

In step $a_7$, when the chlorinated derivative of general formula (XXVII) is treated with an excess of primary amine Y-(Alk')$_m$-NH$_2$ of general formula (XI) for which Alk', Y and m correspond to the definitions for (IF), at high temperature in a suitable solvent such as toluene, the compound of general formula (XXVIII) is obtained.

In step $b_7$, the nitrile function borne by the compound of general formula (XXVIII) is reduced to a primary amine function by catalytic hydrogenation in the presence of Raney nickel and aqueous ammonia to give the compounds of general formula (XXIX). The latter compound is the direct precursor of the compounds of general formula (IF$_4$) in which the different variations of Z are obtained in step $c_7$ according to the processes described in patent application WO 2006/042 955 A1.

Similarly, the chlorinated compounds of general formula (XXVII) allow preparation of the compounds of general formula (IF$_5$), according to Scheme 8.

For the compounds (IF$_5$), Y corresponds to —NR$_7$·R$_8$·—, Q corresponds to S, Alk' corresponds to a linear or branched (C$_1$-C$_5$)alkyl group, k is equal to zero, and m is equal to 1.

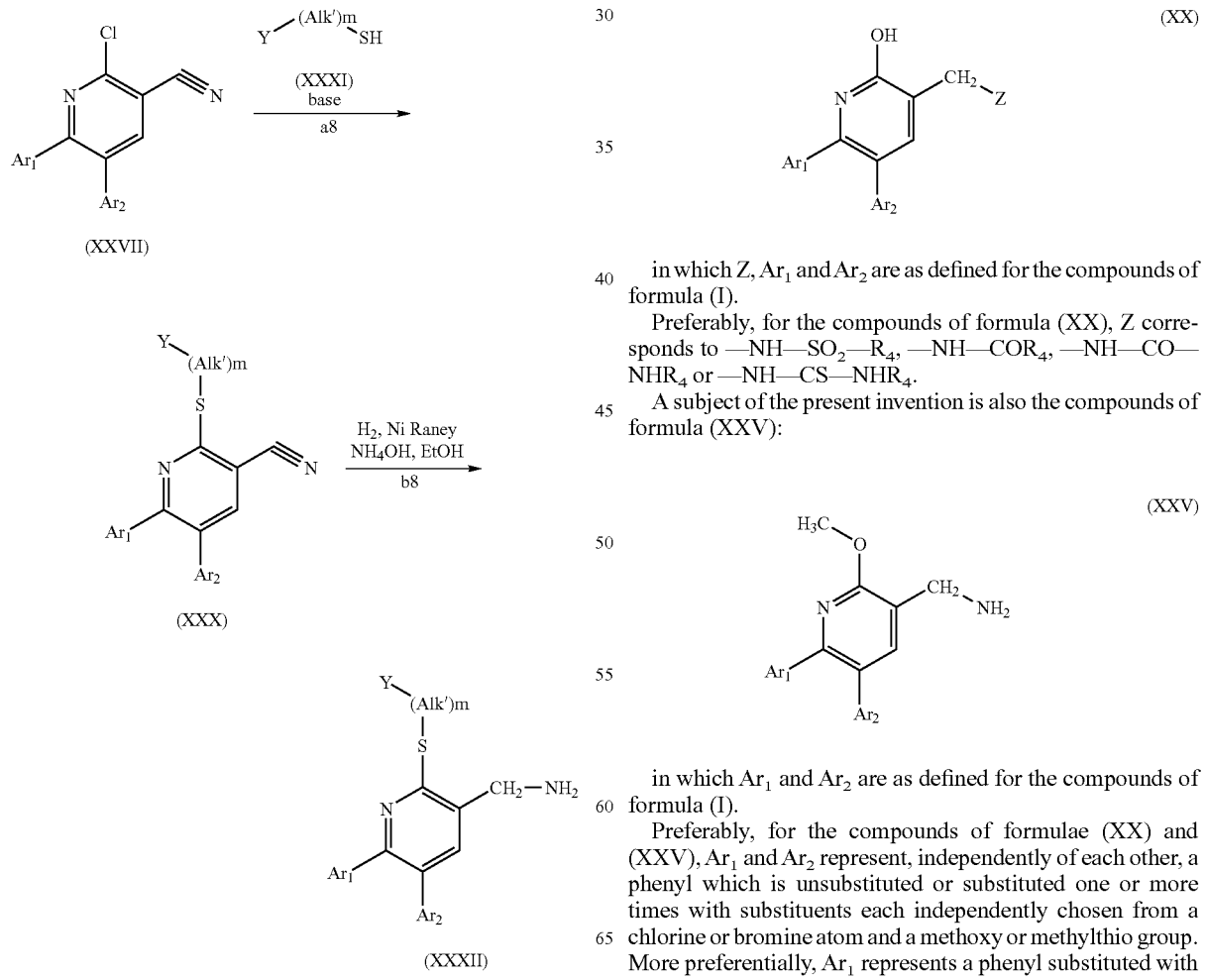

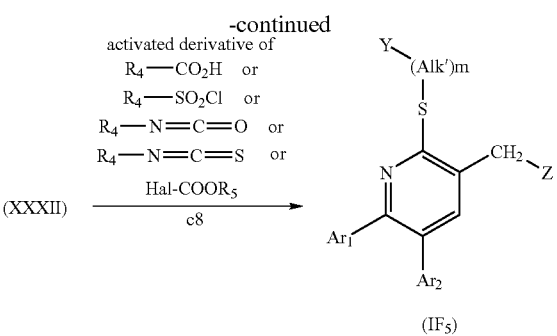

In step $a_8$, the compound of general formula (XXVII) reacts with a thiol (XXXI) of general formula Y-(Alk')$_m$-SH for which Alk', Y and m correspond to the definitions given for (IF), in the presence of a suitable base, for instance potassium carbonate or cesium carbonate, in a solvent such as toluene at high temperature, to give the compounds of general formula (XXXII).

Step $b_8$ is performed under conditions similar to those of step $b_7$ of Scheme 7. The intermediate compounds of formulae (XX) and (XXV) are novel and are used for the preparation of the compounds of formula (I).

A subject of the present invention is also the compounds of formula (XX):

in which Z, Ar$_1$ and Ar$_2$ are as defined for the compounds of formula (I).

Preferably, for the compounds of formula (XX), Z corresponds to —NH—SO$_2$—R$_4$, —NH—COR$_4$, —NH—CO—NHR$_4$ or —NH—CS—NHR$_4$.

A subject of the present invention is also the compounds of formula (XXV):

in which Ar$_1$ and Ar$_2$ are as defined for the compounds of formula (I).

Preferably, for the compounds of formulae (XX) and (XXV), Ar$_1$ and Ar$_2$ represent, independently of each other, a phenyl which is unsubstituted or substituted one or more times with substituents each independently chosen from a chlorine or bromine atom and a methoxy or methylthio group. More preferentially, Ar$_1$ represents a phenyl substituted with a chlorine or bromine atom, and Ar$_2$ represents a phenyl substituted with at least two halogen atoms; the two identical or different halogen atoms being chosen from chlorine and bromine.

The examples that follow describe the preparation of certain compounds in accordance with the invention. These examples are not limiting, and serve merely to illustrate the present invention.

The following abbreviations are used in the preparations and in the Examples:
EtOAc: Ethyl acetate
$BH_3$/DMS: borane-dimethyl sulfide complex
BOC: t-butyloxycarbonyl
DCM: dichloromethane
TLC: thin-layer chromatography
DEAD: diethyl azodicarboxylate
2N hydrochloric ether: 2N solution of hydrogen chloride in diethyl ether
MeOH: methanol
Raney Ni: Raney Nickel®
pyBOP: benzotriazol-1-yloxytris(pyrrolidino)phosphonium hexafluorophosphate
pH 2 buffer solution: solution of 16.66 g of $KHSO_4$ and 32.32 g of $K_2SO_4$ in 1 liter of water
TEA: triethylamine
TFA: trifluoroacetic acid
THF: tetrahydrofuran
The nuclear magnetic resonance spectra are recorded at 250 MHz in DMSO-d6. For the interpretation of the spectra, the following abbreviations are used:
s: singlet, d: doublet, t: triplet, q: quartet, quint: quintet, m: multiplet, bs: broad singlet, dd: doublet of doublet.

The compounds according to the invention are analyzed by HPLC-UV-MS coupling (high performance liquid chromatography—UV detection and mass detection) or HPLC-UV-MS (ultra performance liquid chromatography—UV detection and mass detection). The molecular peak ($MH^+$) and the retention time (rt) in minutes (min) are measured. For HPLC, the machine used is composed of an Agilent HP1100 chromatographic line equipped with an Agilent diode array detector and a mass spectrometer, which is either:—a ZQ Waters single quadrupole mass spectrometer
 a Quattro-Micro Waters triple quadrupole mass spectrometer.
For the HPLC, the machine used is composed of a Waters Acquity HPLC line equipped with a Waters diode array detector and a Waters SQD mass spectrometer.
The analytical conditions are as follows:
Conditions A (HPLC):
A Symmetry Waters® C18 column is used, sold by Waters, of 2.1×50 mm, 3.5 µm, at room temperature, with a flow rate of 0.4 ml/minute.
The eluent is composed as follows:
solvent A: 0.005% trifluoroacetic acid (TFA) in water
solvent B: 0.005% TFA in acetonitrile.
Gradient: The percentage of solvent B ranges from 0 to 90% over 10 minutes with a plateau at 90% B for 5 minutes.
The UV detection is performed at 220 nm and the mass detection in chemical ionization mode, known as positive electrospray (ESI), at atmospheric pressure on a ZQ Waters single quadrupole mass spectrometer.
Conditions B (HPLC):
A Symmetry Waters® C18 column is used, sold by Waters, of 2.1×50 mm, 3.5 µm, at room temperature, with a flow rate of 0.4 ml/minute.
The eluent is composed as follows:
solvent A: 0.005% trifluoroacetic acid (TFA) in water
solvent B: 0.005% TFA in acetonitrile.
Gradient: The percentage of solvent B ranges from 0 to 90% over 20 minutes with a plateau at 90% B for 10 minutes.
The UV detection is performed at 220 nm and the mass detection in chemical ionization mode, known as positive electrospray (ESI), at atmospheric pressure on a ZQ Waters single quadrupole mass spectrometer.
Conditions C(HPLC):
A Symmetry Waters® C18 column is used, sold by Waters, of 2.1×50 mm, 3.5 µm, at room temperature, with a flow rate of 0.4 ml/minute.
The eluent is composed as follows:
solvent A: 10 nM ammonium acetate (pH of about 7)
solvent B: acetonitrile.
Gradient: The percentage of solvent B ranges from 0 to 90% over 10 minutes with a plateau at 90% B for 5 minutes.
The UV detection is performed at 220 nm and the mass detection in chemical ionization mode, known as positive electrospray (ESI), at atmospheric pressure on a Quattro-Micro Waters triple quadrupole mass spectrometer.
Conditions D (HPLC):
An Acquity BEH C18 column of 2.1×50 mm; 1.7 µm is used, at a temperature of 40° C., flow rate of 1 ml/minute.
The eluent is composed as follows:
solvent A: 0.005% TFA in water at about pH 3.1/acetonitrile (97/3)
solvent B: 0.035% TFA in acetonitrile.
Gradient: the percentage of solvent B ranges from 0 to 95% over 2.3 minutes with a plateau at 95% B for 0.6 minute.
The UV detection is performed at 220 nm and the mass detection in chemical ionization mode, referred to as positive electrospray (ESI), is performed at atmospheric pressure on a Waters SQD mass spectrometer.
Mass Spectrometry Conditions
The mass spectra are recorded in positive electrospray (ESI) mode, in order to observe the ions derived from protonation of analyzed compounds ($MH^+$) or from the formation of adducts with other cations such as $Na^+$, $K^+$, etc.
Unless otherwise mentioned, conditions A are the conditions used for LC/MS.

EXAMPLES

Example 1

Compound 4 of Table I

N-{[6-(4-bromophenyl)-5-(2,4-dichlorophenyl)-2-{[(propylsulfonyl)amino]-methyl}pyrid-3-yl]methyl}-4-(trifluoromethyl)benzamide A) 2-{[6-(4-bromophenyl)-5-(2,4-dichlorophenyl)-2-(methoxymethyl)pyrid-3-yl]methyl}-1H-isoindole-1,3(2H)-dione 10.0 g of [6-(4-bromophenyl)-5-(2,4-dichlorophenyl)-2-(methoxymethyl)pyrid-3-yl]methanol obtained according to a procedure similar to that described in application WO 2006/042 955 A1 (preparation 4, steps A to F), 3.57 g of phthalimide and 5.95 g of triphenylphosphine are dissolved in 250 ml of THF. 4.23 g of DEAD are added dropwise at −10° C. and the mixture is then stirred for 5 hours at room temperature.

The reaction medium is diluted with 250 ml of ether. The organic phase is washed with 200 ml of pH 2 buffer solution, with 200 ml of aqueous 10% $NaHCO_3$ solution, with 200 ml of saturated aqueous NaCl solution, and then with 200 ml of distilled water. The resulting phase is dried over $Na_2SO_4$, filtered and then concentrated under reduced pressure.

The crude product thus obtained is purified on silica, eluting with a mixture of DCM/methanol from 0 to 1% over 1 hour.

The fractions containing the purified product are combined and brought to dryness to give 12.0 g of the expected product, which is pure by TLC.

B) 1-[6-(4-bromophenyl)-5-(2,4-dichlorophenyl)-2-(methoxymethyl)pyrid-3-yl]-methanamine 12.0 g of the compound obtained in the preceding step and 1.0 ml of hydrazine hydrate are dissolved in 100 ml of methanol and the mixture is then refluxed for 3 hours. After cooling to room temperature, the reaction medium is brought to dryness and then taken up in 500 ml of DCM and 500 ml of distilled water. The organic phase is extracted with 100 ml of aqueous 10% hydrochloric acid and this acidic phase is washed with 250 ml of DCM.

The aqueous phase is basified with 250 ml of aqueous 10% sodium hydroxide solution and then extracted with 250 ml of DCM. The organic phase is dried over $Na_2SO_4$, filtered and concentrated under reduced pressure to give 6.0 g of expected product.

LC/MS: $MH^+$=450.8; rt=7.24 min;

C) N-{[6-(4-bromophenyl)-5-(2,4-dichlorophenyl)-2-(methoxymethyl)pyrid-3-yl]methyl}-4-(trifluoromethyl)benzamide 2.0 g of the compound obtained in the preceding step, 0.79 g of 4-trifluoromethylbenzoyl chloride and 2.12 ml of triethylamine are dissolved in 50 ml of DCM.

The reaction medium is stirred for 1 hour at room temperature and then washed with 150 ml of distilled water.

The organic phase is dried over $Na_2SO_4$, filtered and concentrated under reduced pressure to give 2.0 g of expected product.

D) LC/MS: $MH^+$=622.8; rt=12.12 min N-{[6-(4-bromophenyl)-5-(2,4-dichlorophenyl)-2-(hydroxymethyl)pyrid-3-yl]methyl}-4-(trifluoromethyl)benzamide 3.5 g of the compound obtained in the preceding step are dissolved in 100 ml of DCM and, at −30° C., 5.6 ml of boron tribromide are then added slowly. The reaction medium is stirred at room temperature for 12 hours and is then washed with 200 ml of distilled water, dried over $Na_2SO_4$, filtered and concentrated under reduced pressure.

In order to remove the traces of brominated product that may form during the reaction, the crude residue is treated in the following manner; the residue is redissolved in 200 ml of a 50/50 v/v dioxane/water mixture and 3.5 g of potassium carbonate are added to the solution. The reaction medium is refluxed for 5 hours, filtered and concentrated under reduced pressure.

The evaporation residue is taken up in 200 ml of DCM. This solution is washed with 200 ml of distilled water, dried over $Na_2SO_4$, filtered and concentrated under reduced pressure to give 2.3 g of expected product.

E) LC/MS: $MH^+$=608.8; rt=18.34 min N-({6-(4-bromophenyl)-5-(2,4-dichlorophenyl)-2-[(1,3-dioxo-1,3-dihydro-2H-isoindol-2-yl)methyl]pyrid-3-yl}methyl)-4-(trifluoromethyl)benzamide 2.3 g of the compound obtained in the preceding step, 0.61 g of phthalimide and 1.2 g of triphenylphosphine are dissolved in 95 ml of THF.

At −10° C., 0.72 g of DEAD is added dropwise and the mixture is then stirred for 5 hours at room temperature.

The reaction medium is diluted with 100 ml of ether. The organic phase is washed with 100 ml of pH 2 buffer solution, with 100 ml of aqueous 10% $NaHCO_3$ solution, with 100 ml of saturated aqueous NaCl solution, and then with 100 ml of distilled water. The resulting phase is dried over $Na_2SO_4$, filtered and then concentrated under reduced pressure.

The crude product thus obtained is purified on silica, eluting with a mixture of DCM/methanol from 0 to 1% over 1 hour.

The fractions containing the purified product are combined and brought to dryness to give 2.2 g of the expected product.

F) LC/MS: $MH^+$=737.8; rt=12.34 min N-{[2-(aminomethyl)-6-(4-bromophenyl)-5-(2,4-dichlorophenyl)pyrid-3-yl]methyl}-4-(trifluoromethyl)benzamide 2.0 g of the compound obtained in the preceding step and 0.3 ml of hydrazine hydrate are dissolved in 50 ml of methanol and the mixture is then refluxed for 3 hours. After cooling to room temperature, the reaction medium is brought to dryness and then taken up in 200 ml of DCM and 200 ml of distilled water. The organic phase is extracted with 50 ml of aqueous 10% hydrochloric acid and this acidic phase is washed with 100 ml of DCM. The aqueous phase is basified with 100 ml of aqueous 10% sodium hydroxide solution and then extracted with 100 ml of DCM. The organic phase is dried over $Na_2SO_4$, filtered and concentrated under reduced pressure to give 1.6 g of expected product.

LC/MS: $MH^+$=607.9; rt=8.26 min

G) N-{[6-(4-bromophenyl)-5-(2,4-dichlorophenyl)-2-{[(propylsulfonyl)amino]-methyl}pyrid-3-yl]methyl}-4-(trifluoromethyl)benzamide 0.3 g of the compound obtained in the preceding step is dissolved in 11 ml of DCM and 0.24 ml of triethylamine and 0.04 ml of n-propanesulfonyl chloride is then added to this solution. The mixture is stirred for 1 hour at room temperature and then diluted with 50 ml of DCM. The organic phase is washed with 100 ml of distilled water, dried over $Na_2SO_4$, filtered and concentrated under reduced pressure to give the crude product. The crude product is purified by chromatography on silica, eluting with a DCM/MeOH gradient of from 0 to 2% MeOH over 1 hour 30 minutes.

The fractions containing the purified product are combined and brought to dryness to give 0.25 g of the expected product in base form.

The purified product is salified in hydrochloride form according to the standard method (dissolution of the base in a solvent such as dichloromethane, addition of 2M hydrochloric ether, evaporation to dryness, uptake of the evaporation residue in a solvent such as dichloromethane, solution poured onto ethyl ether, filtration of the precipitated product, drying). 0.22 g of the expected hydrochloride is obtained.

LC/MS: $MH^+$=714.0; rt=12.02 min

Example 2

Compound 1 of Table I

N-{[6-(4-bromophenyl)-2-[(butyrylamino)methyl]-5-(2,4-dichlorophenyl)pyrid-3-yl]methyl}-4-[(trifluoromethyl)thio]benzamide A) N-{[6-(4-bromophenyl)-5-(2,4-dichlorophenyl)-2-(methoxymethyl)pyrid-3-yl]methyl}-4-[(trifluoromethyl)thio]benzamide 18.0 g of the 1-[6-(4-bromophenyl)-5-(2,4-dichlorophenyl)-2-(methoxymethyl)pyrid-3-yl]methanamine obtained in step B) of Example 1 are dissolved in 200 ml of DCM, followed by addition of 8.38 g of 4-(trifluoromethylthio)benzoic acid, 19.1 ml of triethylamine and 19.63 g of PyBOP.

The medium is stirred for 3 hours at room temperature and is then washed successively with 200 ml of 10% HCl, with 200 ml of aqueous 10% NaHCO$_3$ solution, and then with 200 ml of distilled water.

The organic phase is dried over Na$_2$SO$_4$, filtered and concentrated under reduced pressure to give the crude product. This product is purified by chromatography on silica, eluting with a DCM/MeOH gradient of from 0 to 1% MeOH over 1 hour.

The fractions containing the purified product are combined and brought to dryness to give 18.0 g of expected product.

LC/MS (Conditions C): MH$^+$=654.8; rt=12.12 min

B) N-{[6-(4-bromophenyl)-5-(2,4-dichlorophenyl)-2-(hydroxymethyl)pyrid-3-yl]-methyl}-4-[(trifluoromethyl)thio]benzamide 2.0 g of the compound obtained in the preceding step are dissolved in 100 ml of DCM and, at −30° C., 3.05 ml of boron tribromide are then added slowly. The reaction medium is stirred at room temperature for 12 hours and is then washed with 150 ml of distilled water, dried over Na$_2$SO$_4$, filtered and concentrated under reduced pressure.

In order to remove the traces of brominated product that may form during the reaction, the crude residue is treated in the following manner:

The residue is redissolved in 150 ml of a 50/50 v/v dioxane/water mixture and 2.0 g of potassium carbonate are added to the solution. The reaction medium is refluxed for 5 hours, filtered and concentrated under reduced pressure.

The evaporation residue is taken up in 150 ml of DCM. This solution is washed with 150 ml of distilled water, dried over Na$_2$SO$_4$, filtered and concentrated under reduced pressure to give 1.7 g of expected product.

LC/MS (Conditions B): MH$^+$=640.8; rt=19.15 min

C) N-({6-(4-bromophenyl)-5-(2,4-dichlorophenyl)-2-[(1,3-dioxo-1,3-dihydro-2H-isoindol-2-yl)methyl]pyrid-3-yl}methyl)-4-[(trifluoromethyl)thio]benzamide 4.0 g of N-{[6-(4-bromophenyl)-5-(2,4-dichlorophenyl)-2-(hydroxymethyl)pyrid-3-yl]methyl}-4-[(trifluoromethyl)thio]benzamide obtained in the preceding step are treated following the procedure used in step E) of Example 1, using the following amounts: 1.08 g of phthalimide, 1.68 g of triphenylphosphine and 1.20 g of DEAD, the whole in 100 ml of THF.

3.0 g of expected crude product are obtained.

LC/MS: MH$^+$=769.9; rt=12.69 min

D) N-{[2-(aminomethyl)-6-(4-bromophenyl)-5-(2,4-dichlorophenyl)pyrid-3-yl]-methyl}-4-[(trifluoromethyl)thio]benzamide 3.0 g N-({6-(4-bromophenyl)-5-(2,4-dichlorophenyl)-2-[(1,3-dioxo-1,3-dihydro-2H-isoindol-2-yl)methyl]pyrid-3-yl}methyl)-4-[(trifluoromethyl)thio]benzamide obtained in the preceding step are treated following the procedure used in step F) of Example 1, using the following amounts: 0.2 ml of hydrazine monohydrate in 100 ml of methanol.

2.0 g of expected product are finally obtained.

LC/MS: MH$^+$=639.9; rt=8.56 min

E) N-{[6-(4-bromophenyl)-2-[(butyrylamino)methyl]-5-(2,4-dichlorophenyl)pyrid-3-yl]methyl}-4-[(trifluoromethyl)thio]benzamide 0.25 g of compound obtained in the preceding step is dissolved in 10 ml of DCM. 0.041 g of butyryl chloride and 0.12 ml of triethylamine are added to this solution. The reaction medium is stirred for 1 hour at room temperature, diluted with 50 ml of DCM and then washed with 50 ml of distilled water, followed by 50 ml of 10% HCl, 50 ml of aqueous 10% NaHCO$_3$ solution, and then again with 50 ml of distilled water. The organic phase is dried over Na$_2$SO$_4$, filtered and concentrated under reduced pressure to give the crude product.

This product is purified by chromatography on silica, eluting with a DCM/MeOH gradient of from 0 to 2% MeOH over 1 hour 30 minutes. The fractions containing the purified product are combined and brought to dryness to give the expected product in base form. The purified product is salified in hydrochloride form according to the standard method.

0.14 g of the expected hydrochloride is obtained.

LC/MS: MH$^+$=709.9; rt=12.35 min

Example 3

Compound 8 of Table I

N-{[6-(4-bromophenyl)-5-(2,4-dichlorophenyl)-2-{[(propylcarbamoyl)amino]nethyl}pyrid-3-yl]methyl}-4-[(trifluoromethyl)thio]benzamide 0.25 g of compound obtained in step D) of Example 2 is dissolved in 10 ml of DCM. 0.033 g of n-propyl isocyanate and 0.11 ml of triethylamine are added to this solution. The reaction medium is stirred for 1 hour at room temperature, diluted with 50 ml of DCM and then washed with 50 ml of distilled water, dried over Na$_2$SO$_4$, filtered and concentrated under reduced pressure to give the crude product. This product is purified by chromatography on silica, eluting with a DCM/MeOH gradient of from 0 to 2% MeOH over 1 hour 30 minutes. The fractions containing the purified product are combined and brought to dryness to give the expected product in base form.

The purified product is salified in hydrochloride form according to the standard method. 0.175 g of the expected hydrochloride is obtained.

LC/MS (Conditions B): MH$^+$=725.0; rt=19.73 min

Example 4

Compound 11 of Table I

Propyl({6-(4-bromophenyl)-5-(2,4-dichlorophenyl)-3-[({4-[(trifluoromethyl)thio]benzoyl}amino)methyl]pyrid-2-yl}methyl)carbamate 0.25 g of compound obtained in step D) of Example 2 are dissolved in 10 ml of DCM. 0.047 g of n-propyl chloroformate and 0.11 ml of triethylamine are added to this solution. The reaction medium is stirred for 1 hour at room temperature, diluted with 50 ml of DCM and then washed with 50 ml of distilled water, dried over $Na_2SO_4$, filtered and concentrated under reduced pressure to give the crude product. This product is purified by chromatography on silica, eluting with a DCM/MeOH gradient of from 0 to 2% MeOH over 1 hour 30 minutes.

The fractions containing the purified product are combined and brought to dryness to give 0.16 g of expected product.

LC/MS: $MH^+$=726.0; rt=12.78 min

Example 5

Compound 3 of Table I

N-({6-(4-bromophenyl)-5-(2,4-dichlorophenyl)-2-[(glycoloylamino)methyl]pyrid-3-yl}methyl)-4-[(trifluoromethyl)thio]benzamide 0.250 g of N-{[6-(4-bromophenyl)-5-(2,4-dichlorophenyl)-2-{[(methoxyacetyl)-amino]methyl}pyrid-3-yl]methyl}-4-[(trifluoromethyl)thio]benzamide obtained using a procedure similar to that of Step E of Example 2 is dissolved in 30 ml of DCM. 1.33 ml of boron tribromide are then added slowly, under a nitrogen atmosphere and at −30° C., and the reaction medium is then stirred for 12 hours at room temperature and 100 ml of distilled water and 100 ml of DCM are added. The organic phase is dried over $Na_2SO_4$, filtered and then concentrated under reduced pressure to give the crude product. This product is redissolved in 20 ml of a 50/50 (v/v) dioxane/water mixture to which is added 0.200 g of potassium carbonate. This suspension is refluxed with stirring for 5 hours. The latter operation makes it possible to convert into the expected alcohol the traces of brominated product that may form during the demethylation reaction with $BBr_3$.

After cooling to room temperature, the medium is filtered and the filtrate is then brought to dryness and taken up in 150 ml of DCM.

The organic phase is washed with 100 ml of distilled water, dried over $Na_2SO_4$, filtered and then concentrated under reduced pressure. The crude residue thus obtained is purified by chromatography on silica, eluting with a DCM/MeOH gradient of from 0 to 6% MeOH over 1 hour. The fractions containing the purified product are combined and brought to dryness to give 0.200 g of expected product.

LC/MS: $MH^+$=698.0; rt=11.21 min

Example 6

Compound 13 of Table I)

N-{[6-(4-bromophenyl)-5-(2,4-dichlorophenyl)-2-{[(2-hydroxyethyl)(methyl)amino]methyl}pyrid-3-yl]methyl}-4-(trifluoromethyl)benzamide A) [6-(4-bromophenyl)-5-(2,4-dichlorophenyl)-3-({[4-(trifluoromethyl)benzoyl]amino}methyl)pyrid-2-yl]methyl methanesulfonate 1.0 g of N-{[6-(4-bromophenyl)-5-(2,4-dichlorophenyl)-2-(hydroxymethyl)pyrid-3-yl]methyl}-4-(trifluoromethyl)benzamide, obtained using a procedure similar to that of step B) of Example 2, is dissolved in 50 ml of DCM. 0.43 ml of triethylamine is added to this solution followed, at 0° C., by addition of 0.2 g of methanesulfonyl chloride. The reaction medium is stirred for 1 hour at room temperature, diluted with 50 ml of DCM and then washed with 50 ml of distilled water, dried over $Na_2SO_4$, filtered and concentrated under reduced pressure to give 1.0 g of expected product.

B) N-{[6-(4-bromophenyl)-5-(2,4-dichlorophenyl)-2-{[(2-hydroxyethyl)(methyl)-amino]methyl}pyrid-3-yl]methyl}-4-(trifluoromethyl)benzamide 0.40 g of the compound obtained in the preceding step is dissolved in 20 ml of DCM. 0.048 g of 2-(methylamino)ethanol and 160 μl of triethylamine are added to this solution. The mixture is stirred at room temperature, and 50 ml of distilled water and 50 ml of DCM are then added. The organic phase is dried over $Na_2SO_4$, filtered and concentrated under reduced pressure to give the expected product.

This product is purified by chromatography on silica, eluting with a DCM/MeOH gradient of 0 to 3% MeOH. The fractions containing the purified product are combined and brought to dryness to give the expected product in free base form. This base is salified in hydrochloride form according to the standard method.

0.18 g of the expected hydrochloride is obtained.

LC/MS: $MH^+$=665.9; rt=8.35 minutes.

Example 7

Compound 17 of Table I)

N-{[6-(4-chlorophenyl)-5-(2,4-dichlorophenyl)-3-({[(2-fluorobenzyl)carbamoyl]amino}methyl)pyrid-2-yl]methyl}-2-hydroxyacetamide A) 1-{[6-(4-chlorophenyl)-5-(2,4-dichlorophenyl)-2-(methoxymethyl)pyrid-3-yl]methyl}-3-(2-fluorobenzyl)urea 1.0 g of 1-[6-(4-chlorophenyl)-5-(2,4-dichlorophenyl)-2-(methoxymethyl)pyrid-3-yl]methanamine, obtained according to a procedure similar to that of step B) of Example 1, is dissolved in 20 ml of DCM, to which is added 0.41 g of 2 fluorobenzyl isocyanate. The mixture is stirred at room temperature for 1 hour and then washed with 100 ml of distilled water. The organic phase is dried over $Na_2SO_4$, filtered and concentrated under reduced pressure to give the expected product in crude form. This product is purified by chromatography on silica, eluting with a DCM/MeOH gradient of 0 to 2% MeOH.

The fractions containing the purified product are combined and brought to dryness to give 1.1 g of expected product.
LC/MS: MH+=557.9; rt=10.78 minutes.

B) 1-{[6-(4-chlorophenyl)-5-(2,4-dichlorophenyl)-2-(hydroxymethyl)pyrid-3-yl]-methyl}-3-(2-fluorobenzyl)urea 1.1 g of the compound obtained in the preceding step are treated according to the procedure used in step D) of Example 1, using 3.94 ml of boron tribromide.
After treatment and purification by chromatography on silica (eluting with a DCM/MeOH mixture of 0 to 3% MeOH) and evaporating to dryness, 0.9 g of the expected alcohol is obtained.
LC/MS: MH+=543.9; rt=10.17 minutes C) [6-(4-chlorophenyl)-5-(2,4-dichlorophenyl)-3-({[(2-fluorobenzyl)carbamoyl]-amino}methyl)pyrid-2-yl]methyl methanesulfonate 0.5 g of the compound obtained in the preceding step is treated according to the procedure used in step A) of Example 6, using 0.105 g of methanesulfonyl chloride and 0.15 ml of triethylamine dissolved in 30 ml of DCM. After treatment and evaporation, 0.57 g of expected product is obtained.

D) 1-{[2-(azidomethyl)-6-(4-chlorophenyl)-5-(2,4-dichlorophenyl)pyrid-3-yl]-methyl}-3-(2-fluorobenzyl)urea 0.57 g of the compound obtained in the preceding step is dissolved in 2 ml of DMF, and 0.178 g of sodium azide is added thereto. The mixture is stirred for 12 hours at room temperature and then diluted with 100 ml of distilled water and 100 ml of ethyl ether. The ether phase is washed with 100 ml of an aqueous 10% sodium hydrogen carbonate solution, dried over Na$_2$SO$_4$, filtered and concentrated to dryness to give 0.45 g of expected product.
LC/MS: MH+=569.0; rt=11.35 minutes E) 1-{[2-(aminomethyl)-6-(4-chlorophenyl)-5-(2,4-dichlorophenyl)pyrid-3-yl]-methyl}-3-(2-fluorobenzyl)urea 0.45 g of the compound obtained in the preceding step is dissolved in 10 ml of THF under an atmosphere of dry nitrogen. 0.207 g of triphenylphosphine is added and the reaction medium is stirred at room temperature for 12 hours. 1 ml of water is then added and stirring is continued for a further 12 hours. After evaporating off the solvent, the residue is taken up in 75 ml of distilled water and 75 ml of DCM. The organic phase is dried over Na$_2$SO$_4$, filtered and concentrated under reduced pressure to give the expected product.
This product is purified by chromatography on silica, eluting with a DCM/MeOH gradient of 0 to 7% MeOH. The fractions containing the purified product are combined and brought to dryness to give 0.15 g of expected product.
LC/MS (conditions C): MH+=543.0; rt=9.24 minutes F) N-{[6-(4-chlorophenyl)-5-(2,4-dichlorophenyl)-3-({[(2-fluorobenzyl)-carbamoyl]amino}methyl)pyrid-2-yl]methyl}-2-methoxyacetamide 0.15 g of the amine obtained in the preceding step is acylated using methoxyacetyl chloride according to the procedure used in step E) of Example 2.

To do this, 0.033 g of acid chloride and 88 µl of triethylamine dissolved in 20 ml of DCM are used. After treatment and evaporation of the solvents, 0.1 g of expected product is recovered.

G) N-{[6-(4-chlorophenyl)-5-(2,4-dichlorophenyl)-3-({[(2-fluorobenzyl)-carbamoyl]amino}methyl)pyrid-2-yl]methyl}-2-hydroxyacetamide 0.1 g of the compound obtained in the preceding step is treated according to the procedure used in Example 5, using 0.18 ml of boron tribromide. After treatment, the product is purified by chromatography on silica, eluting with a DCM/MeOH gradient of 0 to 6% MeOH.
The fractions containing the purified product are combined and concentrated to dryness. The free base is salified in hydrochloride form according to the standard method, to give 0.025 g of the expected product.
LC/MS: MH+=601.0; rt=9.70 minutes Example 8

Compound 18 of Table I

N-{[6-(4-chlorophenyl)-5-(2,4-dichlorophenyl)-2-{[(hydroxyacetyl)amino]methyl}pyrid-3-yl]methyl}-4-(trifluoromethyl)benzamide A) N-{[6-(4-chlorophenyl)-5-(2,4-dichlorophenyl)-2-{[(methoxyacetyl)amino]-methyl}pyrid-3-yl]methyl}-4-(trifluoromethyl)benzamide 0.35 g of N-{[6-(4-chlorophenyl)-5-(2,4-dichlorophenyl)-2-{[(methoxyacetyl)amino]methyl}pyrid-3-yl]methyl}-4-(trifluoromethyl)benzamide is prepared from 0.40 g of N-{[2-(aminomethyl)-6-(4-chlorophenyl)-5-(2,4-dichlorophenyl)pyrid-3-yl]methyl}-4-(trifluoromethyl)benzamide and 0.084 g of methoxyacetyl chloride, using a procedure similar to that of step E) of Example 2.

B) N-{[6-(4-chlorophenyl)-5-(2,4-dichlorophenyl)-2-{[(hydroxyacetyl)amino]-methyl}pyrid-3-yl]methyl}-4-(trifluoromethyl)benzamide 0.35 g of the compound obtained in the preceding step is dissolved in 50 ml of DCM. 0.6 ml of boron tribromide is added slowly, under a nitrogen atmosphere and at −30° C., and the reaction medium is then stirred for 12 hours at room temperature. 100 ml of distilled water and 100 ml of DCM are added. The organic phase is dried over Na$_2$SO$_4$, filtered and concentrated under reduced pressure to give the expected product.
This product is purified by chromatography on silica, eluting with a DCM/MeOH gradient of 0 to 5% MeOH. The fractions containing the purified product are combined and concentrated to dryness. The free base thus purified is salified in hydrochloride form according to the standard method to give 0.12 g of the expected product.
LC/MS (conditions D): MH+=622.0; rt=1.94 minutes Example 9

Compound 12 of Table I

N-{[6-(4-bromophenyl)-5-(2,4-dichlorophenyl)-2-({[2-(dimethylamino)ethyl]amino}methyl)pyrid-3-yl]methyl}-4-[(trifluoromethyl)thio]benzamide 0.61 g of N,N-dimethylethylenediamine and 0.288 g of K$_2$CO$_3$ are placed in 20 ml of acetonitrile. The mixture is brought to reflux and 0.5 g of {6-(4-bromophenyl)-5-(2,4-dichlorophenyl)-3-[({4-[(trifluoromethyl)thio]-benzoyl}amino)methyl]pyrid-2-yl}methyl methanesulfonate, obtained according to a procedure similar to that of step A) of Example 6, is then added thereto. The reaction medium is stirred for 4 hours at reflux and then concentrated to dryness under reduced pressure. The evaporation residue is taken up in 150 ml of DCM and 150 ml of distilled water. The organic phase is dried over $Na_2SO_4$, filtered and concentrated under reduced pressure to give the product in crude form. This product is purified by chromatography on silica, eluting with a DCM/MeOH gradient of from 0 to 4% MeOH.

The fractions containing the purified product are combined and brought to dryness to give the expected product in base form. The purified product is salified in hydrochloride form according to the standard method. 0.030 g of the expected hydrochloride is obtained.

LC/MS: $MH^+$=711.0; rt=7.58 min

Example 10

Composition 20 of Table II)

N-{[6-(4-bromophenyl)-5-(2,4-dichlorophenyl)-2-{[2-(dimethylamino)ethoxy]methyl}pyrid-3-yl]methyl}-4-[(trifluoromethyl)thio]benzamide 0.10 g of N,N-dimethylethanolamine and 0.11 g of potassium tert-butoxide are placed in 19 ml of dioxane and the mixture is stirred for 20 minutes at room temperature.

0.6 g of {6-(4-bromophenyl)-5-(2,4-dichlorophenyl)-3-[({4-[(trifluoromethyl)-thio]benzoyl}amino)methyl]pyrid-2-yl}methyl methanesulfonate, obtained according to a procedure similar to that of step A) of Example 6, is dissolved in 4 ml of dioxane and then added to the reaction medium.

Stirring of the reaction medium is continued for 12 hours at room temperature, the medium is then evaporated to dryness and the evaporation residue is taken up in 150 ml of DCM and 150 ml of distilled water.

The organic phase is dried over $Na_2SO_4$, filtered and concentrated under reduced pressure to give the product.

This product is purified by chromatography on silica, eluting with a DCM/MeOH gradient of from 0 to 3% MeOH over 1 hour 30 minutes. The fractions containing the purified product are combined and brought to dryness to give the expected product in base form.

The purified product is salified in hydrochloride form according to the standard method. 0.170 g of the expected hydrochloride is obtained.

LC/MS: $MH^+$=711.9; rt=8.73 min

Example 11

Compound 21 of Table II

[6-(4-bromophenyl)-5-(2,4-dichlorophenyl)-3-({[4-(trifluoromethyl)benzoyl]amino}methyl)pyrid-2-yl]methyl propylcarbamate 0.300 g of the compound obtained in step D) of Example 1 is dissolved in 10 ml of DCM and 0.046 g of n-propyl isocyanate is added thereto. The reaction medium is stirred at room temperature for 2 hours, and 100 ml of distilled water and 100 ml of DCM are then added. The organic phase is washed with 100 ml of distilled water, dried over $Na_2SO_4$, filtered and then concentrated under reduced pressure to give 0.400 g of crude product. This product is purified by chromatography on silica, eluting with a DCM/MeOH gradient of from 0 to 2% MeOH over 1 hour 30 minutes. The fractions containing the purified product are combined and brought to dryness to give 0.15 g of expected product.

LC/MS: $MH^+$=693.8; rt=12.06 min

Example 12

Compound 26 of Table III

N-{[2-(2-aminoethoxy)-6-(4-chlorophenyl)-5-(2,4-dichlorophenyl)pyrid-3-yl]methyl}-4-(trifluoromethyl)benzamide A) 6-(4-chlorophenyl)-5-(2,4-dichlorophenyl)-2-methoxynicotinonitrile 12.6 g of 6-(4-chlorophenyl)-5-(2,4-dichlorophenyl)-2-oxo-1,2-dihydropyridine-3-carbonitrile obtained in a procedure similar to that of application WO/2003 082 191 A1 (step B of Example 1) are dissolved in 48 ml of chloroform. 37.5 g of silver carbonate and then 21 ml of methyl iodide are added and the mixture is refluxed for 12 hours while protected from light. After cooling to room temperature, the reaction medium is filtered. The filtrate is washed with water, dried over $Na_2SO_4$, filtered and brought to dryness to give the crude product.

The expected product is separated from the 6-(4-chlorophenyl)-5-(2,4-dichloro-phenyl)-1-methyl-2-oxo-1,2-dihydropyridine-3-carbonitrile by chromatography on silica, eluting with a DCM//MeOH gradient of from 0 to 1% over 1 hour. The fractions of purified product are combined and concentrated to dryness. 4.33 g of expected product are obtained.

LC/MS: $MH^+$=388.8; rt=12.28 min

B) 1-[6-(4-chlorophenyl)-5-(2,4-dichlorophenyl)-2-methoxypyrid-3-yl]-methanamine 8.7 g of the compound obtained in the preceding step are dissolved in 200 ml of absolute ethanol. 40 ml of 20% aqueous ammonia, 49 ml of distilled water and 4 spatula full of Raney nickel are added to this solution.

After placing in contact with hydrogen, the medium is stirred vigorously until the theoretical volume of gas has been absorbed.

The nickel is then removed by filtration. The solid is rinsed with absolute ethanol and the filtrate is concentrated under reduced pressure to give 8.54 g of crude product.

LC/MS: $MH^+$=392.9; rt=7.53 min

C) N-{[6-(4-chlorophenyl)-5-(2,4-dichlorophenyl)-2-methoxypyrid-3-yl]methyl}-4-(trifluoromethyl)benzamide 4.04 g of the product obtained in the preceding step are dissolved in 68 ml of DCM and 2.39 g of 4-trifluoromethylbenzoic acid, 5.06 ml of triethylamine and 12.32 g of pyBOP are added thereto. After stirring for 3 hours at room temperature, the reaction medium is washed with 100 ml of distilled water, dried over $Na_2SO_4$, filtered and then evaporated to dryness. The crude residue thus obtained is purified a first time on silica, eluting with pure DCM over 1 hour. The purification fractions are combined and brought to dryness to give 5.0 g of purified product.

A 0.5 g aliquot of this product was purified a second time by flash chromatography on a C18 reverse-phase cartridge, eluting with a 75/25 to 85/15 methanol/water mixture over 1 hour 30 minutes. The fractions containing the purified product are combined and concentrated under reduced pressure to give 0.281 g of the expected product.

LC/MS: MH$^+$=564.8; rt=12.62 min

D) D) N-{[6-(4-chlorophenyl)-5-(2,4-dichlorophenyl)-2-hydroxypyrid-3-yl]methyl}-4-(trifluoromethyl)benzamide 4.5 g of the product purified a single time in preceding step are dissolved in 21 ml of acetic acid. 21 ml of hydrobromic acid are added and the reaction medium is refluxed for 15 minutes. After cooling to room temperature, the reaction medium is poured onto 75 ml of aqueous 10% sodium hydroxide at 0° C.

The aqueous phase is extracted with 150 ml of EtOAc. The organic phase thus obtained is washed with 100 ml of distilled water, with 100 ml of saturated NaCl solution, dried over Na$_2$SO$_4$, filtered and concentrated under reduced pressure.

3.81 g of expected product are obtained.

LC/MS: MH$^+$=550.8; rt=10.69 min

E) N-({6-(4-chlorophenyl)-5-(2,4-dichlorophenyl)-2-[2-(1,3-dioxo-1,3-dihydro-2H-isoindol-2-yl)ethoxy]pyrid-3-yl}methyl)-4-(trifluoromethyl)benzamide 1 g of compound obtained in the preceding step is dissolved in 36 ml of toluene. 2.0 g of silver carbonate are added to this solution, followed by addition of 2.32 g of N-(2-bromoethylphthalimide). The reaction medium is stirred at reflux for 48 hours and, after cooling to room temperature, the silver carbonate is then removed by filtration. The filtrate is washed with 150 ml of distilled water, dried over Na$_2$SO$_4$ filtered and then concentrated under reduced pressure to give 1.31 g of expected product.

LC/MS: MH$^+$=723.9; rt=12.81 min

F) N-{[2-(2-aminoethoxy)-6-(4-chlorophenyl)-5-(2,4-dichlorophenyl)pyrid-3-yl]-methyl}-4-(trifluoromethyl)benzamide 0.74 g of compound obtained in the preceding step is dissolved in 6.5 ml of methanol, 0.06 ml of hydrazine monohydrate is added and the mixture is then refluxed for 24 hours. After cooling to room temperature, the reaction medium is brought to dryness. The residue is taken up in 250 ml of water and 250 ml of DCM. The organic phase is extracted with 250 ml of 10% HCl. The acidic aqueous phase is rewashed with 100 ml of DCM and then basified with dilute sodium hydroxide and extracted with 100 ml of DCM.

The organic phase is washed with 100 ml of saturated aqueous NaCl solution, dried over Na$_2$SO$_4$, filtered and then concentrated under reduced pressure to give 0.527 g of expected crude product.

A 0.230 g aliquot of this product was purified by flash chromatography on a C18 reverse-phase cartridge, eluting with a 60/40 to 90/10 methanol/water mixture over 1 hour 30 minutes. The fractions containing the purified product are combined and concentrated under reduced pressure to give 0.069 g of the expected purified product.

LC/MS: MH$^+$=594.0; rt=8.55 min

Example 13

Compound 22 of Table III

N-{[6-(4-chlorophenyl)-5-(2,4-dichlorophenyl)-2-{2-[methylsulfonyl)amino]ethoxy}pyrid-3-yl]methyl}-4-(trifluoromethyl)benzamide 0.4 g of the compound obtained in step F) of Example 12 is dissolved in 13 ml of DCM. 0.1 ml of triethylamine and 0.06 ml of methanesulfonyl chloride are added to this solution and the mixture is stirred for 2 hours at room temperature.

The reaction medium is diluted with 100 ml of DCM and then washed with 100 ml of distilled water.

The organic phase is dried over Na$_2$SO$_4$, filtered and then concentrated under reduced pressure to give 0.411 g of crude product. This product is purified by flash chromatography on a C18 reverse-phase cartridge, eluting with a 75/25 to 85/15 methanol/water mixture over 1 hour.

The fractions containing the purified product are combined and concentrated under reduced pressure to give 0.275 g of the expected purified product.

LC/MS: MH$^+$=671.8; rt=11.83 min

Example 14

Compound 27 of Table III

N-{[6-(4-chlorophenyl)-2-{2-[(cyclopropylcarbonyl)amino]ethoxy}-5-(2,4-dichlorophenyl)pyrid-3-yl]methyl}-4-(trifluoromethyl)benzamide 0.300 g of the compound obtained in F) of Example 12 is dissolved in 13 ml of DCM. 0.053 g of cyclopropanecarboxylic acid, 0.25 ml of triethylamine and 0.318 g of PyBOP are successively added to this solution. The reaction medium is stirred at room temperature for 3 hours, and 100 ml of distilled water and 100 ml of DCM are then added. The organic phase is washed with 100 ml of distilled water, dried over Na$_2$SO$_4$, filtered and then concentrated under reduced pressure to give 0.500 g of crude product.

This product is purified by flash chromatography on a C18 reverse-phase cartridge, eluting with a 60/40 to 80/20 methanol/water mixture over 1 hour and then an 80/20 plateau for further 1 hour. The fractions containing the purified product are combined and concentrated under reduced pressure to give 0.231 g of the expected purified product.

LC/MS: MH$^+$=661.9; rt=12.09 min

Tables I, II and III below indicate the characteristics of the compounds prepared above and also of compounds prepared via similar preparation methods.

Thus, the tables that follow illustrate the chemical structures and the physical properties of compounds according to the invention.

In the tables below, nC$_3$H$_7$ and iC$_3$H$_7$ represent, respectively, a propyl group and an isopropyl group.

TABLE I

[Structure: pyridine core with substituents — 2-(4-Hal-phenyl), 3-(2,4-dichlorophenyl), 6-CH2-N(R1)-(Alk')m-Y, 5-CH2-Z]

| Compound No. | Salt | Prepared according to | (Alk')m | Y | Z | R1 | Hal | rt (min) | MH+ | LCMS conditions |
|---|---|---|---|---|---|---|---|---|---|---|
| 1 | HCl | Ex 2 | m = 0 | —CO—nC3H7 | —NH—C(O)—C6H4—SCF3 | H | Br | 12.35 | 709.9 | A |
| 2 | HCl | Ex 2 | m = 0 | —CO—CH2—OCH3 | —NH—C(O)—C6H4—SCF3 | H | Br | 12.03 | 711.9 | A |
| 3 | HCl | Ex 5 | m = 0 | —CO—CH2OH | —NH—C(O)—C6H4—SCF3 | H | Br | 11.21 | 698.0 | A |
| 4 | HCl | Ex 1 | m = 0 | —SO2—nC3H7 | —NH—C(O)—C6H4—CF3 | H | Br | 12.02 | 714.0 | A |
| 5 | HCl | Ex 1 | m = 0 | —SO2—C6H4—CF3 | —NH—C(O)—C6H4—CF3 | H | Br | 12.65 | 815.9 | A |
| 6 | HCl | Ex 1 | m = 0 | —SO2—CH2—C6H4—CF3 | —NH—C(O)—C6H4—CF3 | H | Br | 20.84 | 829.9 | B |
| 7 | / | Ex 1 | m = 0 | —SO2—CH3 | —NH—C(O)—C6H4—SCF3 | H | Br | 19.25 | 717.9 | B |
| 8 | HCl | Ex 3 | m = 0 | —CO—NH—nC3H7 | —NH—C(O)—C6H4—SCF3 | H | Br | 19.73 | 725.0 | B |

TABLE I-continued

[Structure: pyridine core with substituents — at position 2: phenyl-Hal (para); at position 3: 2,4-dichlorophenyl; at position 5: CH2-Z; at position 6: CH2-N(R1)-(Alk')m-Y]

| Compound No. | Salt | Prepared according to | (Alk')m | Y | Z | R1 | Hal | rt (min) | MH+ | LCMS conditions |
|---|---|---|---|---|---|---|---|---|---|---|
| 9 | / | Ex 3 | m = 0 | —CO—NH—C6H5 (phenyl) | —NH—C(O)—C6H4—S—CF3 (para) | H | Br | 20.57 | 759.0 | B |
| 10 | / | Ex 3 | m = 0 | —CS—NH—nC3H7 | —NH—C(O)—C6H4—CF3 (para) | H | Br | 19.9 | 708.9 | B |
| 11 | / | Ex 4 | m = 0 | —CO—O—nC3H7 | —NH—C(O)—C6H4—S—CF3 (para) | H | Br | 12.78 | 726.0 | A |
| 12 | HCl | Ex 9 | m = 1 and Alk' = (CH2)2 | —N(CH3)2 | —NH—C(O)—C6H4—S—CF3 (para) | H | Br | 7.58 | 711.0 | A |
| 13 | HCl | Ex 6 | m = 1 and Alk' = (CH2)2 | —OH | —NH—C(O)—C6H4—CF3 (para) | CH3 | Br | 8.35 | 665.9 | A |
| 14 | HCl | Ex 6 | m = 1 and Alk' = (CH2) | —CO—NH2 | —NH—C(O)—C6H4—CF3 (para) | CH3 | Br | 8.36 | 678.9 | A |
| 15 | HCl | Ex 6 | m = 1 and Alk' = (CH2)2 | —SO2—CH3 | —NH—C(O)—C6H4—CF3 (para) | CH3 | Br | 8.71 | 727.9 | A |

TABLE I-continued

| Compound No. | Salt | Prepared according to | (Alk')m | Y | Z | R₁ | Hal | rt (min) | MH+ | LCMS conditions |
|---|---|---|---|---|---|---|---|---|---|---|
| 16 | HCl | Ex 5 | m = 0 | —CO—CH₂OH | (N-methyl 4-(trifluoromethylthio)benzamide) | H | Cl | 11.08 | 653.9 | A |
| 17 | HCl | Ex 7 | m = 0 | —CO—CH₂OH | (N-methyl N'-(2-fluorobenzyl)urea) | H | Cl | 9.70 | 601.0 | A |
| 18 | HCl | Ex 8 | m = 0 | —CO—CH₂OH | (N-methyl 4-(trifluoromethyl)benzamide) | H | Cl | 1.94 | 622.0 | D |
| 19 | HCl | Ex 8 | m = 0 | —CO—(CH₂)₂—OH | (N-methyl 4-(trifluoromethyl)benzamide) | H | Cl | 1.86 | 636.0 | D |

TABLE II

[Structure: pyridine with 2-(4-bromophenyl), 3-(2,4-dichlorophenyl), 6-CH2-O-(Alk')m-Y, and 5-CH2-Z substituents]

| Compound No. | Salt | Prepared according to | m and Alk' | Y | Z | tr (min) | MH+ | LCMS conditions |
|---|---|---|---|---|---|---|---|---|
| 20 | HCl | Ex 10 | m = 1 and Alk' = (CH₂)₂ | —N(CH₃)₂ | [4-(SCF₃)-benzamide with N-methyl linker] | 8.73 | 711.9 | A |
| 21 | / | Ex 11 | m = 0 | —CO—NH—nC₃H₇ | [4-(CF₃)-benzamide with N-methyl linker] | 12.06 | 693.8 | A |

TABLE III

[Structure: pyridine with 2-(4-chlorophenyl), 3-(2,4-dichlorophenyl), 6-O-(Alk')m-Y, and 5-CH2-Z substituents]

| Compound No. | Salt | Prepared according to | m and Alk' | Y | Z | rt (min) | MH+ | LCMS conditions |
|---|---|---|---|---|---|---|---|---|
| 22 | / | Ex 13 | m = 1 and Alk' = (CH₂)₂ | —NH—SO₂—CH₃ | [4-(CF₃)-benzamide with N-methyl linker] | 11.83 | 671.8 | A |
| 23 | / | Ex 13 | m = 1 and Alk' = (CH₂)₃ | —NH—SO₂—CH₃ | [4-(CF₃)-benzamide with N-methyl linker] | 11.88 | 686.0 | A |

TABLE III-continued

| Compound No. | Salt | Prepared according to | m and Alk' | Y | Z | rt (min) | MH+ | LCMS conditions |
|---|---|---|---|---|---|---|---|---|
| 24 | / | Ex 13 | m = 1 and Alk' = (CH₂)₂ | —NH—SO₂—iC₃H₇ | 4-CF₃-benzamide | 20.03 | 700.0 | B |
| 25 | / | Ex 13 | m = 1 and Alk' = (CH₂)₂ | —NH—SO₂—CH₃ | 4-SCF₃-benzamide | 12.19 | 703.8 | A |
| 26 | / | Ex 12 | m = 1 and Alk' = (CH₂)₂ | —NH₂ | 4-CF₃-benzamide | 8.55 | 594.0 | A |
| 27 | / | Ex 14 | m = 1 and Alk' = (CH₂)₂ | —NH—CO—cyclopropyl | 4-CF₃-benzamide | 12.09 | 661.9 | A |

The NMR analyses for compounds 3, 13 to 19 are given below:

Compound 3
RMN$^1$H: DMSO-d$_6$ (250 MHz) δ (ppm): 3.91: s: 2H; 4.64: d: 2H; 4.70: d: 2H; 7.25: d; 2H; 7.34: d: 1H; 7.47: dd: 1H; 7.51: d: 2H; 7.66: d: 1H; 7.71: s: 1H; 7.84: d: 2H; 8.01: d: 2H; 8.41: t: 1H; 9.30: t: 1H.

Compound 13
RMN$^1$H: DMSO-d$_6$ (250 MHz) δ (ppm): 3.00-3.14: m: 3H; 3.29-3.54: m: 2H; 3.76-3.96: m: 2H; 4.62: d: 2H; 4.74-5.09: m: 2H; 5.37: sl: 1H; 7.28 7.41: m: 3H; 7.46-7.61: m: 3H; 7.71: d: 1H; 7.86: d: 2H; 7.90: s: 1H; 8.12: d: 2H; 9.53: t: 1H; 9.69: sl: 1H.

Compound 14
RMN$^1$H: DMSO-d$_6$ (250 MHz) δ (ppm): 3.05: s: 3H; 3.94-4.29: m: 2H; 4.62: d: 2H; 4.80-5.08: m: 2H; 7.29: d: 2H; 7.35: d: 1H; 7.46-7.58: m: 3H; 7.71: d: 1H; 7.77: s: 1H; 7.86: d: 2H; 7.90: s: 1H; 8.04: s: 1H; 8.11: d: 2H; 9.52: t: 1H; 9.74: sl: 1H.

Compound 15
RMN$^1$H: DMSO-d$_6$ (250 MHz) δ (ppm): 3.05: s: 3H; 3.11: s: 3H; 3.81-3.93: m: 4H; 4.63: d: 2H; 4.88-5.14: m: 2H; 7.30-7.40: m: 3H; 7.45-7.59: m: 3H; 7.70: d: 1H; 7.85: s: 1H; 7.89: d: 2H; 8.14: d: 2H; 9.57: t: 1H; 10.28: si: 1H.

Compound 16
RMN$^1$H: DMSO-d$_6$ (250 MHz) δ (ppm): 3.91: s: 2H; 4.65: d: 2H; 4.71: d: 2H; 7.26-7.42: m: 5H; 7.47: dd: 1H; 7.67: d: 1H; 7.71: s: 1H; 7.84: d: 2H; 8.01: d: 2H; 8.41: t: 1H; 9.30: t: 1H.

Compound 17
RMN$^1$H: DMSO-d$_6$ (250 MHz) δ (ppm): 3.90: s: 2H; 4.21-4.31: m: 2H; 4.35-4.43: m: 2H; 4.60: d: 2H; 6.58: sl: 1H; 6.68: sl: 1H; 6.98-7.18: m: 2H; 7.33: s: 7H; 7.50: dd: 1H; 7.58: s: 1H; 7.70: d: 1H; 8.38: t: 1H.

Compound 18
RMN$^1$H: DMSO-d$_6$ (250 MHz) δ (ppm): 3.91: d: 2H; 4.66: d: 2H; 4.71: d: 2H; 5.66: t: 1H; 7.26-7.43: m: 5H; 7.47: dd: 1H; 7.67: d: 1H; 7.70: s: 1H; 7.88: d: 2H; 8.09: d: 2H; 8.42: t: 1H; 9.34: t: 1H.

Compound 19
RMN$^1$H DMSO-d$_6$ (250 MHz) δ (ppm): 2.36: t: 2H; 3.66: t: 2H; 3.72-3.85: m: 2H; 4.65: t: 2H; 7.27-7.42: m: 5H; 7.44: dd: 1H; 7.64-7.71: m: 2H; 7.88: d: 2H; 8.10: d: 2H; 8.42: t: 1H; 9.35: t: 1H.

The compounds of formula (I) show very good affinity in vitro (IC$_{50}$≦5.10$^{-7}$M) for the CB$_1$ cannabinoid receptors under the experimental conditions described by M. Rinaldi-Carmona et al. (FEBS Letters, 1994, 350, 240-244).

The antagonist nature of the compounds of formula (I) was demonstrated by means of the results obtained in models of inhibition of adenylate cyclase as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The interaction of a compound according to the invention with the $CB_1$ receptors present in the brain is determined in mice by means of the test of ex vivo binding of [3H]-CP55940 after intravenous injection or oral administration as described in M. Rinaldi-Carmona et al., FEBS Letters, 1994, 350, 240-244 and M. Rinaldi-Carmona et al., Life Sciences, 1995, 56, 1941-1947, M. Rinaldi-Carmona et al., J. Pharmacol. Exp. Ther., 2004, 310, 905-914.

The interaction of a compound according to the invention with the $CB_1$ receptors present peripherally is determined in mice by means of the test of reversion of the inhibitory effect of CP55940 on gastrointestinal transit after oral administration, as described in M. Rinaldi-Carmona et al., J. Pharmacol. Exp. Ther., 2004, 310, 905-914.

The compounds of formula (I) are compatible with their use as medicaments.

Thus, according to another of its aspects, a subject of the invention is medicaments for human or veterinary medicine, which comprise a compound of formula (I) or an addition salt thereof with a pharmaceutically acceptable acid.

Thus, the compounds according to the invention may be used in man or animals (especially mammals including, in a non-limiting manner, dogs, cats, horses, cattle and sheep), in the treatment or prevention of diseases involving the $CB_1$ cannabinoid receptors.

For example, and in a non-limiting manner, the compounds of formula (I) are useful as psychotropic medicaments, especially for treating psychiatric disorders including anxiety, depression, mood disorders, insomnia, delirium disorders, obsessive disorders, psychoses in general, schizophrenia, attention deficit and hyperactivity (ADH) disorders in hyperactive children, and also for treating disorders associated with the use of psychotropic substances, especially in the case of substance abuse and/or substance dependency, including alcohol dependency and nicotine dependency.

The compounds of formula (I) according to the invention may be used as medicaments for treating migraine, stress, diseases of psychosomatic origin, panic attacks, epilepsy, movement disorders, in particular dyskinesia or Parkinson's disease, trembling and dystonia.

The compounds of formula (I) according to the invention may also be used as medicaments in the treatment of memory disorders, cognitive disorders, in particular in the treatment of senile dementia and Alzheimer's disease, and also in the treatment of attention or alertness disorders.

Furthermore, the compounds of formula (I) may be useful as neuroprotective agents, in the treatment of ischaemia, cranial trauma and the treatment of acute or chronic neurodegenerative diseases: including chorea, Huntington's chorea and Tourette's syndrome.

The compounds of formula (I) according to the invention may be used as medicaments in the treatment of pain: neuropathic pain, acute peripheral pain, chronic pain of inflammatory origin, pain induced by an anticancer treatment.

The compounds of formula (I) according to the invention may be used as medicaments in human or veterinary medicine in the prevention and treatment of appetite disorders, appetence disorders (for sugars, carbohydrates, drugs, alcohol or any appetizing substance) and/or eating behavior, especially for the treatment of obesity or bulimia, and also for the treatment of type II diabetes or non-insulin-dependent diabetes and for the treatment of dyslipidemia and metabolic syndrome. Thus, the compounds of formula (I) according to the invention are useful in the treatment of obesity and of the risks associated with obesity, especially the cardiovascular risks.

Furthermore, the compounds of formula (I) according to the invention may be used as medicaments in the treatment and prevention of gastrointestinal disorders, diarrheic disorders, ulcers, vomiting, vesical and urinary disorders, liver diseases of alcoholic or non-alcoholic origin such as chronic cirrhosis, fibrosis, hepatic steatosis and steatohepatitis; and also disorders of endocrine origin, cardiovascular disorders, hypotension, atherosclerosis, hemorrhagic shock, septic shock, asthma, chronic bronchitis, chronic obstructive pulmonary diseases, Raynaud's syndrome, glaucoma, fertility disorders, premature labor, interruption of pregnancy, inflammatory phenomena, immune system diseases, in particular autoimmune and neuroinflammatory diseases such as rheumatoid arthritis, rectional arthritis, diseases resulting in demyelinization, multiple sclerosis, infectious and viral diseases such as encephalitis, strokes, and also as medicaments for anticancer chemotherapy, for the treatment of Guillain-Barré syndrome and for the treatment of bone diseases and osteoporosis. Furthermore, the compounds of formula (I) according to the invention may be used for their protective effects against drug-induced cardiotoxicity.

According to the present invention, the compounds of formula (I) are most particularly useful for the preparation of medicaments that are useful for preventing and treating psychiatric disorders, in particular schizophrenia, attention and alertness disorders, attention deficit and hyperactivity (ADH) disorders in hyperactive children; for preventing and treating memory deficiencies and cognitive disorders; dependence on and weaning from a substance, in particular alcohol dependency, nicotine dependency, weaning from alcohol and weaning from tobacco; acute or chronic neurodegenerative diseases.

More particularly, the compounds of formula (I) according to the present invention are useful in the preparation of medicaments that are useful for treating and preventing appetite disorders, appetence disorders, metabolic disorders, obesity, type II diabetes, metabolic syndrome, dyslipidemia, the gastrointestinal disorders, inflammatory phenomena, immune system diseases, psychotic disorders, alcohol dependency and nicotine dependency.

According to one of its aspects, the present invention relates to the use of a compound of formula (I) or pharmaceutically acceptable salts thereof for treating the disorders and diseases indicated above.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the said compound, and also at least one pharmaceutically acceptable excipient.

The said excipients are chosen, according to the pharmaceutical form and the desired mode of administration, from the usual excipients known to those skilled in the art.

The pharmaceutical compositions according to the present invention may contain, along with a compound of formula (I), one (or more) other active principle that is useful in the treatment of the disorders and diseases indicated above.

Thus, a subject of the present invention is also pharmaceutical compositions containing a compound of formula (I)

according to the present invention combined with one (or more) active principle chosen from one of the following therapeutic classes:

another antagonist or allosteric modulator of the cannabinoid $CB_1$ receptors;
a cannabinoid $CB_2$ receptor modulator;
an angiotensin II $AT_1$ receptor antagonist;
a converting enzyme inhibitor;
a calcium antagonist;
a diuretic;
a beta-blocker;
an antihyperlipemiant or an antihypercholesterolaemiant;
an antidiabetic agent;
another anti-obesity agent or agent acting on metabolic disorders;
a nicotine agonist or a partial nicotine agonist;
an antidepressant, an antipsychotic agent or an anxiolytic agent;
an anticancer agent or an antiproliferative agent;
an opioid antagonist;
and also:
an agent for improving the memory;
an agent that is useful in the treatment of alcoholism or the symptoms of weaning;
an agent that is useful for treating osteoporosis;
a non-steroidal or steroidal anti-inflammatory drug;
an anti-infectious agent;
an analgesic;
an antiasthmatic agent.

According to another aspect of the invention, the compound of formula (I), or a pharmaceutically acceptable salt thereof or a solvate thereof, and the other combined active principle may be administered simultaneously, separately or sequentially over time.

The term "simultaneous use" means the administration of the compounds of the composition according to the invention included in the same pharmaceutical form.

The term "separate use" means the administration, at the same time, of the two compounds of the composition according to the invention, each included in a separate pharmaceutical form.

The term "use sequentially over time" means the successive administration of the first compound of the composition of the invention, included in one pharmaceutical form, and then of the second compound of the composition according to the invention, included in a separate pharmaceutical form. In this case, the time elapsed between the administration of the first compound of the composition according to the invention and the administration of the second compound of the same composition according to the invention generally does not exceed 24 hours.

In the pharmaceutical compositions of the present invention for oral, sublingual subcutaneous, intramuscular, intravenous, topical, local, intratracheal, intranasal, transdermal or rectal administration, the active principle of formula (I) above, or the possible salt thereof, may be administered in a unit form of administration, as a mixture with standard pharmaceutical excipients, to man and animals for the prophylaxis or treatment of the above disorders or diseases.

The appropriate unit forms of administration include oral-route forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---:|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may be from 0.01 to 100 mg/kg in one or more dosage intakes, preferentially 0.02 to 50 mg/kg.

There may be particular cases in which higher or lower dosages are appropriate; such dosages do not depart from the context of the invention. According to the usual practice, the dosage that is appropriate to each patient is determined by the doctor according to the mode of administration and the weight and response of the said patient.

According to another of its aspects, the present invention also relates to a method for treating the pathologies indicated above, which comprises the administration to a patient of an effective dose of a compound according to the invention.

What is claimed is:
1. A compound of formula (I):

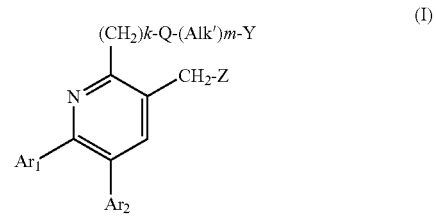

in which:
Q represents an oxygen atom, a sulfur atom or a radical —$NR_1$— in which $R_1$ represents a hydrogen atom or a group ($C_1$-$C_4$)alkyl;
Z represents a group —$N(R_3)XR_4$, —$N(R_3)COOR_5$ or —$OCON(R_3)R_5$, wherein
X represents a group —CO—, —$SO_2$—, —$CON(R_6)$— or —$CSN(R_6)$—;
$R_3$ represents a hydrogen atom or a group ($C_1$-$C_4$)alkyl;
$R_4$ represents:
a non-aromatic ($C_3$-$C_{12}$) carbocyclic radical, which is unsubstituted or substituted one or more times with identical or different substituents chosen from a group ($C_1$-$C_4$)alkyl, hydroxyl, ($C_1$-$C_4$)alkoxy, ($C_1$-$C_4$)alkylthio and cyano;
a saturated or unsaturated, oxygen-bearing, sulfur-bearing or nitrogen-bearing heterocyclic radical of 3 to 8 atoms, which is unsubstituted or substituted with one or more identical or different substituents chosen from a halogen atom, a group ($C_1$-$C_4$)alkyl, hydroxyl, trifluoromethyl, ($C_1$-$C_4$)alkoxy, trifluoromethoxy, trifluoromethylthio, ($C_1$-$C_4$)alkylthio, cyano, nitro and an oxo group;
an indolyl which is unsubstituted or substituted with a halogen atom, a group ($C_1$-$C_4$)alkyl, trifluoromethyl, hydroxyl, ($C_1$-$C_4$)alkoxy, trifluoromethoxy, trifluoromethylthio, ($C_1$-$C_4$)alkylthio, cyano or nitro;

a tetrahydronaphthyl; a naphthyl;

a benzothiophenyl or a benzofuryl;

a phenyl which is unsubstituted or substituted one or more times with identical or different substituents chosen from a halogen atom, a group $(C_1-C_4)$alkyl, trifluoromethyl, trifluoromethoxy, hydroxyl, $(C_1-C_4)$alkoxy, $(C_1-C_4)$alkylthio, trifluoromethylthio, cyano, nitro, $(C_1-C_4)$alkanoyl, phenyl or a group $S(O)_n$Alk, $OS(O)_n$Alk or $NR_7R_8$;

a benzodioxyl;

a phenoxymethylene or a 1-phenoxyethylene, the phenyl groups being unsubstituted or substituted one or more times with identical or different substituents chosen from a halogen atom, a group $(C_1-C_4)$alkyl, trifluoromethyl, trifluoromethoxy, hydroxyl, $(C_1-C_4)$alkoxy, $(C_1-C_4)$alkylthio, trifluoromethylthio, cyano, nitro, $(C_1-C_4)$alkanoyl, phenyl or a group $S(O)_n$Alk, $OS(O)_n$Alk or $NR_7R_8$; the methylene or ethylene groups being unsubstituted or substituted one or more times with identical or different substituents chosen from a group $(C_1-C_4)$alkyl or with a $(C_3-C_7)$cycloalkyl;

a phenylcyclopropyl, the phenyl group being unsubstituted or substituted one or more times with identical or different substituents chosen from a halogen atom, a group $(C_1-C_4)$alkyl, trifluoromethyl, trifluoromethoxy, hydroxyl, $(C_1-C_4)$alkoxy, $(C_1-C_4)$alkylthio, trifluoromethylthio, cyano, nitro, $(C_1-C_4)$alkanoyl, phenyl or a group $S(O)_n$Alk, $OS(O)_n$Alk or $NR_7R_8$;

a $(C_1-C_2)$alkylene substituted with one or two identical or different substituents chosen from:

(i) a $C_3-C_{12}$ non-aromatic carbocyclic radical which is unsubstituted or substituted one or more times with a group $(C_1-C_4)$alkyl, which may be identical or different;

(ii) a phenyl which is unsubstituted or substituted with one or more substituents, which may be identical or different, chosen from a halogen atom, a group $(C_1-C_4)$alkyl, hydroxyl, trifluoromethyl, $(C_1-C_4)$alkoxy, $(C_1-C_4)$alkylthio, trifluoromethoxy, trifluoromethylthio, $(C_1-C_4)$alkanoyl, cyano, nitro, phenyl or a group $S(O)_n$Alk, $OS(O)_n$Alk or $NR_7R_8$;

(iii) a saturated or unsaturated, oxygen-bearing, sulfur-bearing or nitrogen-bearing heterocyclic radical of 3 to 8 atoms, which is unsubstituted or substituted with one or more substituents, which may be identical or different, chosen from a halogen atom, a group $(C_1-C_4)$alkyl, hydroxyl, trifluoromethyl, $(C_1-C_4)$alkoxy, trifluoromethoxy, trifluoromethylthio, $(C_1-C_4)$alkylthio, cyano or nitro;

with the proviso that, when X represents a group —CON$(R_6)$— or —CSN$(R_6)$—, $R_4$ is a group $(C_1-C_6)$alkanoyl or a benzoyl or benzylcarbonyl group, the phenyl group of the said groups being unsubstituted or substituted with one or more identical or different substituents chosen from a halogen atom, a group $(C_1-C_4)$alkyl, trifluoromethyl, trifluoromethoxy, hydroxyl, $(C_1-C_4)$alkoxy, $(C_1-C_4)$alkylthio, trifluoromethylthio, cyano, nitro, $(C_1-C_4)$alkanoyl, phenyl or a group $S(O)_n$Alk, $OS(O)_n$Alk or $NR_7R_8$;

$R_5$ represents a phenyl which is unsubstituted or substituted one or more times with identical or different substituents chosen from a halogen atom or a group $(C_1-C_4)$alkyl, trifluoromethyl, trifluoromethoxy, cyano, nitro, $(C_1-C_4)$alkoxy, $(C_1-C_4)$alkylthio, trifluoromethylthio, a group $S(O)_n$Alk, $OS(O)_n$Alk or $NR_7R_8$;

$R_6$ represents a hydrogen atom or a group $(C_1-C_4)$alkyl;

or $R_4$ and $R_6$, together with the nitrogen atom to which they are attached, constitute a heterocyclic radical of 3 to 8 atoms, optionally containing a second heteroatom chosen from an oxygen, sulfur or nitrogen atom, which is unsubstituted or substituted one or more times with identical or different substituents chosen from a group $(C_1-C_4)$alkyl; a group $(C_1-C_4)$alkanoyl; a group $NR_7R_8$ or $CONR_7R_8$, a phenyl group; the said phenyl group being unsubstituted or substituted one or more times with identical or different substituents chosen from a halogen atom, a group $(C_1-C_4)$alkyl, $(C_1-C_4)$alkoxy or trifluoromethyl, $(C_1-C_4)$alkylthio, trifluoromethoxy, trifluoromethylthio or a group $OS(O)_n$Alk, $S(O)_n$Alk or $NR_7R_8$;

$R_7$ and $R_8$ represent, independently of each other, a hydrogen atom, a group $(C_1-C_4)$alkyl or $R_7$ and $R_8$, together with the nitrogen atom to which they are attached, constitute a saturated heterocyclic radical of 4 to 8 atoms possibly containing another heteroatom chosen from a nitrogen, oxygen or sulfur atom;

$Ar_1$ and $Ar_2$ represent, independently of each other, a phenyl which is unsubstituted or substituted one or more times with identical or different substituents chosen from a halogen atom, a group $(C_1-C_6)$alkyl, $(C_1-C_6)$alkoxy, $(C_1-C_6)$alkylthio, trifluoromethyl, trifluoromethoxy, trifluoromethylthio, cyano, nitro, a group $S(O)_n$Alk, $OS(O)_n$Alk or $NR_7R_8$;

Y represents a group —$R_{1'}$, —$OR_{5'}$, —$N(R_{3'})X'R_{4'}$, —$N(R_{3'})COOR_{5'}$, —$NR_7R_8$, —$CON(R_{3'})R_{5'}$, —CSN$(R_{3'}R_{5'}$, —$C(O)R_{2'}$, —$C(O)$—O—$R_{2'}$, —$SO_2R_{2'}$, —$SO_2N(R_{3'})R_5$ or —$OCON(R_{3'})R_{5'}$;

$R_{1'}$ represents a radical —CN or a saturated or unsaturated, oxygen-bearing, sulfur-bearing or nitrogen-bearing heterocyclic radical of 3 to 8 atoms, possibly containing a second heteroatom chosen from nitrogen, oxygen and sulfur, which is unsubstituted or substituted with one or more identical or different substituents chosen from a halogen atom, a group $(C_1-C_4)$alkyl, hydroxyl, trifluoromethyl, $(C_1-C_4)$alkoxy, trifluoromethoxy, trifluoromethylthio, $(C_1-C_4)$alkylthio, cyano, nitro or with an oxo group;

X' represents a group —CO—, —$SO_2$—, —CON$(R_{6'})$— or —CSN$(R_{6'})$—;

$R_{2'}$ represents:

a group $(C_1-C_{10})$alkyl, which is unsubstituted or substituted with a substituent chosen from $CF_3$, $(C_1-C_4)$alkoxy and hydroxyl;

a non-aromatic $(C_3-C_{12})$ carbocyclic radical, which is unsubstituted or substituted one or more times with identical or different substituents chosen from a halogen atom, a group $(C_1-C_4)$alkyl, hydroxyl, trifluoromethyl, $(C_1-C_4)$alkoxy, a phenyl which is unsubstituted or substituted one or more times with identical or different substituents chosen from a halogen atom, a group $(C_1-C_4)$alkyl, trifluoromethyl, trifluoromethoxy, cyano, nitro, $(C_1-C_4)$alkoxy, $(C_1-C_4)$alkylthio, trifluoromethylthio, $S(O)_n$Alk or $OS(O)_n$Alk;

a benzyl which is unsubstituted or substituted one or more times with identical or different substituents chosen from a halogen atom, a group $(C_1-C_4)$alkyl, trifluoromethyl, trifluoromethoxy, cyano, nitro, $(C_1-C_4)$alkoxy, $(C_1-C_4)$alkylthio, trifluoromethylthio, $S(O)_n$Alk or $OS(O)_n$Alk;

$R_{3'}$ represents a hydrogen atom or a group $(C_1-C_4)$alkyl;

$R_{4'}$ represents:

a group $(C_1-C_{10})$alkyl, which is unsubstituted or substituted with a group $CF_3$;

a non-aromatic ($C_3$-$C_{12}$) carbocyclic radical, which is unsubstituted or substituted one or more times with identical or different substituents chosen from a group ($C_1$-$C_4$)alkyl, hydroxyl, a halogen atom, a trifluoromethyl, ($C_1$-$C_4$)alkoxy, ($C_1$-$C_4$)alkylthio or cyano;

a saturated or unsaturated, oxygen-bearing, sulfur-bearing or nitrogen-bearing heterocyclic radical of 3 to 8 atoms, which is unsubstituted or substituted with one or more identical or different substituents chosen from a halogen atom, a group ($C_1$-$C_4$)alkyl, hydroxyl, trifluoromethyl, ($C_1$-$C_4$)alkoxy, trifluoromethoxy, trifluoromethylthio, ($C_1$-$C_4$)alkylthio, cyano, nitro and an oxo group;

an indolyl which is unsubstituted or substituted with a halogen atom, a group ($C_1$-$C_4$)alkyl, trifluoromethyl, hydroxyl, ($C_1$-$C_4$)alkoxy, trifluoromethoxy, trifluoromethylthio, ($C_1$-$C_4$)alkylthio, cyano or nitro;

a tetrahydronaphthyl; a naphthyl;

a benzothiophenyl or a benzofuryl;

a phenyl which is unsubstituted or substituted one or more times with identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group S(O)$_n$Alk, OS(O)$_n$Alk or NR$_7$R$_8$;

a benzodioxyl;

a phenoxymethylene or a 1-phenoxyethylene, the phenyl groups being unsubstituted or substituted one or more times with identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group S(O)$_n$Alk, OS(O)$_n$Alk or NR$_7$R$_8$; the methylene or ethylene groups being unsubstituted or substituted one or more times with a group ($C_1$-$C_4$)alkyl or with a ($C_3$-$C_7$)cycloalkyl;

a phenylcyclopropyl, the phenyl group being unsubstituted or substituted one or more times with identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group S(O)$_n$Alk, OS(O)$_n$Alk or NR$_7$R$_8$;

a ($C_1$-$C_2$)alkylene substituted with one or two identical or different substituents chosen from:

(i) a $C_3$-$C_{12}$ non-aromatic carbocyclic radical which is unsubstituted or substituted one or more times with a group ($C_1$-$C_4$)alkyl;

(ii) a phenyl which is unsubstituted or substituted with one or more substituents, which may be identical or different, chosen from a halogen atom, a group ($C_1$-$C_4$)alkyl, hydroxyl, trifluoromethyl, ($C_1$-$C_4$)alkoxy, ($C_1$-$C_4$)alkylthio, trifluoromethoxy, trifluoromethylthio, ($C_1$-$C_4$)alkanoyl, cyano, nitro, phenyl or a group S(O)$_n$Alk, OS(O)$_n$Alk or NR$_7$R$_8$;

(iii) a saturated or unsaturated, oxygen-bearing, sulfur-bearing or nitrogen-bearing heterocyclic radical of 3 to 8 atoms, which is unsubstituted or substituted with one or more substituents, which may be identical or different, chosen from a halogen atom, a group ($C_1$-$C_4$)alkyl, hydroxyl, trifluoromethyl, ($C_1$-$C_4$)alkoxy, trifluoromethoxy, trifluoromethylthio, ($C_1$-$C_4$)alkylthio, cyano or nitro;

with the proviso that, when X' represents a group —CON(R$_6$— or —CSN(R$_{6'}$)—, R$_{4'}$ is a group ($C_1$-$C_6$)alkanoyl or a benzoyl or benzylcarbonyl group, the phenyl group of the said groups being unsubstituted or substituted with identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group S(O)$_n$Alk, OS(O)$_n$Alk or NR$_7$R$_8$;

R$_{5'}$ represents:

a hydrogen atom;

a group ($C_1$-$C_{10}$)alkyl, which is unsubstituted or substituted with a group CF$_3$;

a non-aromatic ($C_3$-$C_{12}$) carbocyclic radical, which is unsubstituted or substituted one or more times with identical or different substituents chosen from a halogen atom, a group ($C_1$-$C_4$)alkyl, hydroxyl, trifluoromethyl or ($C_1$-$C_4$)alkoxy;

a phenyl which is unsubstituted or substituted one or more times with identical or different substituents chosen from a halogen atom, a group ($C_1$-$C_4$)alkyl, trifluoromethyl, trifluoromethoxy, cyano, nitro, ($C_1$-$C_4$)alkoxy, ($C_1$-$C_4$)alkylthio, trifluoromethylthio, S(O)$_n$Alk, OS(O)$_n$Alk or NR$_7$R$_8$;

or R$_{3'}$ and R$_{5'}$ together with the nitrogen atom to which they are attached, constitute a heterocyclic radical of 3 to 8 atoms, optionally containing a second heteroatom chosen from an oxygen, sulfur or nitrogen atom, which is unsubstituted or substituted one or more times with identical or different substituents chosen from a halogen atom, a trifluoromethyl, a group ($C_1$-$C_4$)alkyl, a phenyl group or a group NR$_7$R$_8$, a group CONR$_7$R$_8$; the said group ($C_1$-$C_4$)alkyl being unsubstituted or substituted with a trifluoromethyl group; and the said phenyl group being unsubstituted or substituted one or more times with a halogen atom, a group ($C_1$-$C_4$)alkyl, ($C_1$-$C_4$)alkoxy, trifluoromethyl, ($C_1$-$C_4$)alkylthio, trifluoromethoxy, trifluoromethylthio, OS(O)$_n$Alk or S(O)$_n$Alk;

R$_{6'}$ represents a hydrogen atom or a group ($C_1$-$C_4$)alkyl;

or R$_{4'}$ and R$_{6'}$ together with the nitrogen atom to which they are attached, constitute a heterocyclic radical of 3 to 8 atoms, optionally containing a second heteroatom chosen from an oxygen, sulfur or nitrogen atom, which is unsubstituted or substituted one or more times with identical or different substituents chosen from a group ($C_1$-$C_4$)alkyl, a phenyl group, a halogen atom, a hydroxyl, trifluoromethyl, ($C_1$-$C_4$)alkoxy, trifluoromethoxy, trifluoromethylthio, ($C_1$-$C_4$)alkylthio, an oxo group, ($C_1$-$C_4$)alkanoyl, NR$_7$R$_8$ or CONR$_7$R$_8$; the said group ($C_1$-$C_4$)alkyl being unsubstituted or substituted with a trifluoromethyl group; and the said phenyl group being unsubstituted or substituted one or more times with identical or different substituents chosen from a halogen atom, a group ($C_1$-$C_4$)alkyl, ($C_1$-$C_4$)alkoxy, trifluoromethyl, ($C_1$-$C_4$)alkylthio, trifluoromethoxy, trifluoromethylthio, OS(O)$_n$Alk or S(O)$_n$Alk;

R$_{7'}$ and R$_{8'}$ represent, independently of each other, a hydrogen atom, a group ($C_1$-$C_4$)alkyl or R$_{7'}$ and R$_{8'}$, together with the nitrogen atom to which they are attached, constitute a saturated heterocyclic radical of 4 to 8 atoms possibly containing another heteroatom chosen from a nitrogen, oxygen or sulfur atom;

Alk represents a linear or branched ($C_1$-$C_7$)alkyl group;

Alk' represents a linear or branched ($C_1$-$C_5$)alkyl group;

n represents 0, 1 or 2;

k represents 1; and m represents 0 or 1;

or a salt thereof.

2. The compound of formula (I) according to claim 1, wherein:

Y represents a group —C(O)R$_{2'}$, —SO$_2$R$_{2'}$; —CON(R$_{3'}$)R$_{5'}$, —CSNR$_3$R$_{5'}$, —C(O)—O—R$_{2'}$, —NR$_7$R$_{8'}$, —OR$_{5'}$ or —R$_{1'}$;

k represents 1;

Q represents the radical NR$_1$ wherein R$_1$ is a hydrogen atom or a methyl group; and Alk' represents a linear (C$_2$-C$_4$)alkyl group;

or a salt thereof.

3. The compound according to claim 2, wherein:

R$_{2'}$ represents:

a group (C$_1$-C$_{10}$)alkyl, which is unsubstituted or substituted with a substituent chosen from CF$_3$, (C$_1$-C$_4$)alkoxy and hydroxyl;

a non-aromatic (C$_3$-C$_{12}$) carbocyclic radical, which is unsubstituted or substituted one or more times with identical or different substituents chosen from a halogen atom, a group (C$_1$-C$_4$)alkyl, (C$_1$-C$_4$)alkoxy, hydroxyl and trifluoromethyl;

a phenyl which is unsubstituted or substituted one or more times with identical or different substituents chosen from a halogen atom, a group (C$_1$-C$_4$)alkyl, trifluoromethyl, trifluoromethoxy, (C$_1$-C$_4$)alkoxy, (C$_1$-C$_4$)alkylthio and trifluoromethylthio;

a benzyl which is unsubstituted or substituted one or more times with identical or different substituents chosen from a halogen atom, a group (C$_1$-C$_4$)alkyl, trifluoromethyl, trifluoromethoxy, (C$_1$-C$_4$)alkoxy, (C$_1$-C$_4$)alkylthio and trifluoromethylthio;

R$_{3'}$ represents a hydrogen atom or a group (C$_1$-C$_4$)alkyl;

R$_{5'}$ represents:

a hydrogen atom;

a group (C$_1$-C$_{10}$)alkyl, which is unsubstituted or substituted with a group CF$_3$;

a non-aromatic (C$_3$-C$_{12}$) carbocyclic radical, which is unsubstituted or substituted one or more times with identical or different substituents chosen from a halogen atom, a group (C$_1$-C$_4$)alkyl, hydroxyl, trifluoromethyl, (C$_1$-C$_4$)alkoxy;

a phenyl which is unsubstituted or substituted one or more times with identical or different substituents chosen from a halogen atom, a group (C$_1$-C$_4$)alkyl, trifluoromethyl, trifluoromethoxy, (C$_1$-C$_4$)alkoxy, (C$_1$-C$_4$)alkylthio or trifluoromethylthio;

R$_{3'}$ and R$_{5'}$, together with the nitrogen atom to which they are attached, constitute a heterocyclic radical of 3 to 8 atoms, possibly containing a second heteroatom chosen from an oxygen, sulfur or nitrogen atom, which is unsubstituted or substituted one or more times with identical or different substituents chosen from a halogen atom, a trifluoromethyl or a group (C$_1$-C$_4$)alkyl, which is unsubstituted or substituted with a trifluoromethyl; and R$_{7'}$ and R$_{8'}$ represent, independently of each other, a hydrogen atom or a group (C$_1$-C$_4$)alkyl, or R$_{7'}$ and R$_{8'}$, together with the nitrogen atom to which they are attached, constitute a saturated heterocyclic radical of 4 to 8 atoms possibly containing another heteroatom chosen from a nitrogen, oxygen or sulfur atom;

or a salt thereof.

4. The compound of formula (I) according to claim 1, wherein:

Y represents —C(O)R$_{2'}$, —SO$_2$R$_{2'}$, or —CONHR$_{5'}$;

or a salt thereof.

5. The compound of formula (I) according to claim 1, wherein:

Y representing a group —SO$_2$R$_{2'}$, —CON(R$_{3'}$)R$_{5'}$, —NR$_7$R$_{8'}$, —OR$_{5'}$, or —SO$_2$N(R$_{3'}$)R$_{5'}$;

k represents 1;

Q represents an oxygen atom; and

Alk' represents a linear (C$_2$-C$_4$)alkyl group;

or a salt thereof.

6. The compound according to claim 5, wherein:

R$_{2'}$ represents:

a group (C$_1$-C$_{10}$)alkyl, which is unsubstituted or substituted with a substituent chosen from CF$_3$, (C$_1$-C$_4$)alkoxy and hydroxyl;

a (C$_3$-C$_{12}$) non-aromatic carbocyclic group, which is unsubstituted or substituted one or more times with identical or different substituents chosen from a halogen atom, a group (C$_1$-C$_4$)alkyl, hydroxyl, trifluoromethyl, (C$_1$-C$_4$)alkoxy;

a phenyl which is unsubstituted or substituted one or more times with identical or different substituents chosen from a halogen atom, a group (C$_1$-C$_4$)alkyl, trifluoromethyl, trifluoromethoxy, (C$_1$-C$_4$)alkoxy, (C$_1$-C$_4$)alkylthio and trifluoromethylthio;

R$_{3'}$ represents a hydrogen atom or a group (C$_1$-C$_4$)alkyl;

R$_{5'}$ represents:

a hydrogen atom;

a group (C$_1$-C$_{10}$)alkyl, which is unsubstituted or substituted with a group CF$_3$;

a non-aromatic (C$_3$-C$_{12}$) carbocyclic radical, which is unsubstituted or substituted one or more times with identical or different substituents chosen from a halogen atom, a group (C$_1$-C$_4$)alkyl, hydroxyl, trifluoromethyl or (C$_1$-C$_4$)alkoxy;

a phenyl which is unsubstituted or substituted one or more times with identical or different substituents chosen from a halogen atom, a group (C$_1$-C$_4$)alkyl, trifluoromethyl, trifluoromethoxy, (C$_1$-C$_4$)alkoxy, (C$_1$-C$_4$)alkylthio and trifluoromethylthio;

R$_{3'}$ and R$_{5'}$, together with the nitrogen atom to which they are attached, constitute a heterocyclic radical of 3 to 8 atoms, possibly containing a second heteroatom chosen from an oxygen, sulfur or nitrogen atom, which is unsubstituted or substituted one or more times with identical or different substituents chosen from a halogen atom, a trifluoromethyl or a group (C$_1$-C$_4$)alkyl, which is unsubstituted or substituted with a trifluoromethyl; and R$_{7'}$ and R$_{8'}$ represent, independently of each other, a hydrogen atom, a group (C$_1$-C$_4$)alkyl or R$_{7'}$ and R$_{8'}$, together with the nitrogen atom to which they are attached, constitute a saturated heterocyclic radical of 4 to 8 atoms possibly containing another heteroatom chosen from a nitrogen, oxygen or sulfur atom;

or a salt thereof.

7. The compound of formula (I) according to claim 1, wherein:

Z represents —N(R$_3$)COR$_4$, —N(R$_3$)SO$_2$R$_4$, or —N(R$_3$)CON(R$_6$)R$_4$;

or a salt thereof.

8. The compound of formula (I) according to claim 1, which is selected from the group consisting of:

N-{[6-(4-bromophenyl)-5-(2,4-dichlorophenyl)-2-{[(hydroxyacetyl)amino]methyl}pyrid-3-yl]methyl}-4-[(trifluoromethyl)thio]benzamide;

N-{[6-(4-bromophenyl)-5-(2,4-dichlorophenyl)-2-{[(2-hydroxyethyl)(methyl)amino]methyl}pyrid-3-yl]methyl}-4-(trifluoromethyl)benzamide;

N-{[2-{[(2-amino-2-oxoethyl)(methyl)amino]methyl}-6-(4-bromophenyl)-5-(2,4-dichlorophenyl)pyrid-3-yl]methyl}-4-(trifluoromethyl)benzamide;

N-{[6-(4-bromophenyl)-5-(2,4-dichlorophenyl)-2-({methyl [2-(methylsulfonyl)-ethyl]amino}methyl)pyrid-3-yl]methyl}-4-(trifluoromethyl)benzamide;

N-{[6-(4-chlorophenyl)-5-(2,4-dichlorophenyl)-2-{[(hydroxyacetyl)amino]methyl}pyrid-3-yl]methyl}-4-[(trifluoromethyl)thio]benzamide;

N-{[6-(4-chlorophenyl)-5-(2,4-dichlorophenyl)-3-({[(2-fluorobenzyl)carbamoyl]-amino}methyl)pyrid-2-yl]methyl}-2-hydroxyacetamide;

N-{[6-(4-chlorophenyl)-5-(2,4-dichlorophenyl)-2-{[(hydroxyacetyl)amino]methyl}pyrid-3-yl]methyl}-4-(trifluoromethyl)benzamide; and N-{[6-(4-chlorophenyl)-5-(2,4-dichlorophenyl)-2-{[(3-hydroxypropanoyl)amino]-methyl}pyrid-3-yl]methyl}-4-(trifluoromethyl)benzamide;

or a salt thereof.

9. The compound of formula (I) according to claim 8, which is selected from the group consisting of:

N-{[6-(4-bromophenyl)-5-(2,4-dichlorophenyl)-2-{[(hydroxyacetyl)amino]methyl}pyrid-3-yl]methyl}-4-[(trifluoromethyl)thio]benzamide;

N-{[6-(4-chlorophenyl)-5-(2,4-dichlorophenyl)-2-{[(hydroxyacetyl)amino]methyl}pyrid-3-yl]methyl}-4-[(trifluoromethyl)thio]benzamide;

N-{[6-(4-chlorophenyl)-5-(2,4-dichlorophenyl)-3-({[(2-fluorobenzyl)carbamoyl]-amino}methyl)pyrid-2-yl]methyl}-2-hydroxyacetamide; and N-{[6-(4-chlorophenyl)-5-(2,4-dichlorophenyl)-2-{[(hydroxyacetyl)amino]methyl}pyrid-3-yl]methyl}-4-(trifluoromethyl)benzamide;

or a salt thereof.

10. A compound of formula (XX):

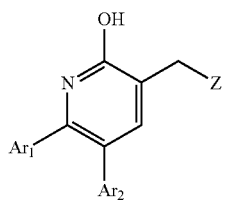

(XX)

in which

Z represents a group —N($R_3$)X$R_4$, —N($R_3$)COO$R_5$ or —OCON($R_3$)$R_5$, wherein X represents a group —CO—, —SO$_2$—, —CON($R_6$)— or —CSN($R_6$)—;

$R_3$ represents a hydrogen atom or a group ($C_1$-$C_4$)alkyl;

$R_4$ represents:

a non-aromatic ($C_3$-$C_{12}$) carbocyclic radical, which is unsubstituted or substituted one or more times with identical or different substituents chosen from a group ($C_1$-$C_4$)alkyl, hydroxyl, ($C_1$-$C_4$)alkoxy, ($C_1$-$C_4$)alkylthio and cyano;

a saturated or unsaturated, oxygen-bearing, sulfur-bearing or nitrogen-bearing heterocyclic radical of 3 to 8 atoms, which is unsubstituted or substituted with one or more identical or different substituents chosen from a halogen atom, a group ($C_1$-$C_4$)alkyl, hydroxyl, trifluoromethyl, ($C_1$-$C_4$)alkoxy, trifluoromethoxy, trifluoromethylthio, ($C_1$-$C_4$)alkylthio, cyano, nitro and an oxo group;

an indolyl which is unsubstituted or substituted with a halogen atom, a group ($C_1$-$C_4$)alkyl, trifluoromethyl, hydroxyl, ($C_1$-$C_4$)alkoxy, trifluoromethoxy, trifluoromethylthio, ($C_1$-$C_4$)alkylthio, cyano or nitro;

a tetrahydronaphthyl; a naphthyl;

a benzothiophenyl or a benzofuryl;

a phenyl which is unsubstituted or substituted one or more times with identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group S(O)$_n$Alk, OS(O)$_n$Alk or N$R_7R_8$;

a benzodioxyl;

a phenoxymethylene or a 1-phenoxyethylene, the phenyl groups being unsubstituted or substituted one or more times with identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group S(O)$_n$Alk, OS(O)$_n$Alk or N$R_7R_8$; the methylene or ethylene groups being unsubstituted or substituted one or more times with identical or different substituents chosen from a group ($C_1$-$C_4$) alkyl or with a ($C_3$-$C_7$)cycloalkyl;

a phenylcyclopropyl, the phenyl group being unsubstituted or substituted one or more times with identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group S(O)$_n$Alk, OS(O)$_n$Alk or N$R_7R_8$;

a ($C_1$-$C_2$)alkylene substituted with one or two identical or different substituents chosen from:

(i) a $C_3$-$C_{12}$ non-aromatic carbocyclic radical which is unsubstituted or substituted one or more times with a group ($C_1$-$C_4$)alkyl, which may be identical or different;

(ii) a phenyl which is unsubstituted or substituted with one or more substituents, which may be identical or different, chosen from a halogen atom, a group ($C_1$-$C_4$)alkyl, hydroxyl, trifluoromethyl, ($C_1$-$C_4$)alkoxy, ($C_1$-$C_4$)alkylthio, trifluoromethoxy, trifluoromethylthio, ($C_1$-$C_4$)alkanoyl, cyano, nitro, phenyl or a group S(O)$_n$Alk, OS(O)$_n$Alk or N$R_7R_8$;

(iii) a saturated or unsaturated, oxygen-bearing, sulfur-bearing or nitrogen-bearing heterocyclic radical of 3 to 8 atoms, which is unsubstituted or substituted with one or more substituents, which may be identical or different, chosen from a halogen atom, a group ($C_1$-$C_4$)alkyl, hydroxyl, trifluoromethyl, ($C_1$-$C_4$)alkoxy, trifluoromethoxy, trifluoromethylthio, ($C_1$-$C_4$)alkylthio, cyano or nitro;

with the proviso that, when X represents a group —CON($R_6$)— or —CSN($R_6$)—, $R_4$ is a group ($C_1$-$C_6$)alkanoyl or a benzoyl or benzylcarbonyl group, the phenyl group of the said groups being unsubstituted or substituted with one or more identical or different substituents chosen from a halogen atom, a group ($C_1$-$C_4$)alkyl, trifluoromethyl, trifluoromethoxy, hydroxyl, ($C_1$-$C_4$)alkoxy, ($C_1$-$C_4$)alkylthio, trifluoromethylthio, cyano, nitro, ($C_1$-$C_4$)alkanoyl, phenyl or a group S(O)$_n$Alk, OS(O)$_n$Alk or N$R_7R_8$;

$R_5$ represents a phenyl which is unsubstituted or substituted one or more times with identical or different substituents chosen from a halogen atom or a group ($C_1$-$C_4$) alkyl, trifluoromethyl, trifluoromethoxy, cyano, nitro, ($C_1$-$C_4$)alkoxy, ($C_1$-$C_4$)alkylthio, trifluoromethylthio, a group S(O)$_n$Alk, OS(O)$_n$Alk or NR$_7$R$_8$;

$R_6$ represents a hydrogen atom or a group ($C_1$-$C_4$)alkyl;

or $R_4$ and $R_6$, together with the nitrogen atom to which they are attached, constitute a heterocyclic radical of 3 to 8 atoms, optionally containing a second heteroatom chosen from an oxygen, sulfur or nitrogen atom, which is unsubstituted or substituted one or more times with identical or different substituents chosen from a group ($C_1$-$C_4$)alkyl; a group ($C_1$-$C_4$)alkanoyl; a group NR$_7$R$_9$ or CONR$_7$R$_8$, a phenyl group; the said phenyl group being unsubstituted or substituted one or more times with identical or different substituents chosen from a halogen atom, a group ($C_1$-$C_4$)alkyl, ($C_1$-$C_4$)alkoxy or trifluoromethyl, ($C_1$-$C_4$)alkylthio, trifluoromethoxy, trifluoromethylthio or a group OS(O)$_n$Alk, S(O)$_n$Alk or NR$_7$R$_8$;

$R_7$ and $R_8$ represent, independently of each other, a hydrogen atom, a group ($C_1$-$C_4$)alkyl or $R_7$ and $R_8$, together with the nitrogen atom to which they are attached, constitute a saturated heterocyclic radical of 4 to 8 atoms possibly containing another heteroatom chosen from a nitrogen, oxygen or sulfur atom;

Ar$_1$ and Ar$_2$ represent, independently of each other, a phenyl which is unsubstituted or substituted one or more times with identical or different substituents chosen from a halogen atom, a group ($C_1$-$C_6$)alkyl, ($C_1$-$C_6$)alkoxy, ($C_1$-$C_6$)alkylthio, trifluoromethyl, trifluoromethoxy, trifluoromethylthio, cyano, nitro, a group S(O)$_n$Alk, OS(O)$_n$Alk or NR$_7$R$_8$;

Alk represents a linear or branched ($C_1$-$C_7$)alkyl group; and n represents 0, 1 or 2.

11. The compound according to claim 10, wherein Z represents —NH—SO$_2$—R$_4$, —NH—COR$_4$, —NH—CO—NHR$_4$ or —NH—CS—NHR$_4$.

12. A pharmaceutical composition comprising a compound of formula (I) according to claim 1 or a pharmaceutically acceptable salt thereof and at least one pharmaceutically acceptable excipient.

13. A pharmaceutical composition comprising a compound of formula (I) according to claim 3 or a pharmaceutically acceptable salt thereof and at least one pharmaceutically acceptable excipient.

14. A pharmaceutical composition comprising a compound of formula (I) according to claim 8 or a pharmaceutically acceptable salt thereof and at least one pharmaceutically acceptable excipient.

15. A pharmaceutical composition comprising a compound of formula (I) according to claim 9 or a pharmaceutically acceptable salt thereof and at least one pharmaceutically acceptable excipient.

* * * * *